United States Patent
Schmidt et al.

(10) Patent No.: US 7,056,659 B1
(45) Date of Patent: *Jun. 6, 2006

(54) CHARACTERIZING NUCLEIC ACIDS

(75) Inventors: Günter Schmidt, Houghton (GB); Andrew Hugin Thompson, Alloway (GB)

(73) Assignee: Xzillion GmbH & Co., Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/462,408

(22) PCT Filed: Jul. 13, 1998

(86) PCT No.: PCT/GB98/02048

§ 371 (c)(1),
(2), (4) Date: Apr. 10, 2000

(87) PCT Pub. No.: WO99/02728

PCT Pub. Date: Jan. 21, 1999

(30) Foreign Application Priority Data

| Jul. 11, 1997 | (GB) | 9714715.1 |
| Jul. 11, 1997 | (GB) | 9714717.7 |
| Sep. 10, 1997 | (GB) | 9719284.3 |

(51) Int. Cl.
*C12Q 1/68* (2006.01)
*C12P 19/34* (2006.01)
*C07H 21/04* (2006.01)
*B01D 57/02* (2006.01)

(52) U.S. Cl. .................. 435/6; 435/91.1; 435/91.2; 536/23.1; 536/24.3; 536/25.3; 204/451

(58) Field of Classification Search .................. 435/6, 435/91.2, 91.1; 536/24.3, 25.3, 23.1; 204/451
See application file for complete search history.

(56) References Cited

U.S. PATENT DOCUMENTS

| 5,302,509 | A | | 4/1994 | Cheeseman | |
| 5,547,835 | A | * | 8/1996 | Koster | 435/6 |
| 5,716,812 | A | * | 2/1998 | Withers et al. | 435/74 |
| 6,027,890 | A | * | 2/2000 | Ness et al. | 435/6 |
| 6,270,976 | B1 | * | 8/2001 | Schmidt et al. | 435/6 |
| 6,287,780 | B1 | * | 9/2001 | Schmidt et al. | 435/6 |
| 6,297,017 | B1 | * | 10/2001 | Schmidt et al. | 435/6 |
| 6,312,904 | B1 | * | 11/2001 | Schmidt et al. | 435/6 |
| 2003/0194717 | A1 | * | 10/2003 | Schmidt et al. | 435/6 |

FOREIGN PATENT DOCUMENTS

| WO | WO 95/04160 | 2/1995 |
| WO | WO96/32504 | 10/1996 |
| WO | WO 96/33205 | 10/1996 |
| WO | WO 97/27331 | 7/1997 |

OTHER PUBLICATIONS

Alberts et al. Molecular Biology of the Cell, 1994, p. 298.*
Smith, L.M. "High speed DNA sequencing by capillary gel electrophoresis", 1991, Nature, 349: 812-813.*
Dubiley et al. "Fractionation, phosphorylation and ligation on oligonucleotide microchips to enhance sequencing by hybridization" Nucleic Acids Reserch, Jun. 1997, 25(12): 2259-2265.*

* cited by examiner

*Primary Examiner*—B J Forman
(74) *Attorney, Agent, or Firm*—Buchanan Ingersoll PC

(57) ABSTRACT

A method for characterizing DNA, which comprises: (i) providing a population of DNA fragments, each fragment having cleavably attached thereto a mass label for identifying a feature of that fragment; (ii) separating the fragments on the basis of their length; (iii) cleaving each fragment in a mass spectrometer to release its mass label; and (iv) determining each mass label by mass spectrometry to relate the feature of each fragment to the length of the fragment.

24 Claims, 14 Drawing Sheets

BAND 1

BAND 2

BAND 3

ORTHOGONAL TOF GEOMETRY

| BANDS | | | | | | |
|---|---|---|---|---|---|---|
| 1 | C | C | A | A | | |
| 2 | | C | A | A | C | |
| 3 | | | A | A | C | T |
| FINAL | C | C | A | A | C | T |

FIG. 15

CHARACTERIZING NUCLEIC ACIDS

The present invention relates to a method for characterising DNA, especially to obtain sequence information.

Conventional DNA sequencing uses a DNA polymerase to add numerous dideoxy/deoxynucleotides to an oligonucleotide primer, annealed to a single stranded DNA template, in a template specific manner. Random termination of this process is achieved when terminating nucleotides, i.e. the dideoxynucleotides, are incorporated in the template complement. In this way, a series of fragments is produced containing all possible lengths of the template complement. A 'DNA ladder' is produced when the randomly terminated strands are separated on a denaturing polyacrylamide gel. Sequence information is gathered, following polyacrylamide gel electrophoresis, by detecting the 'DNA ladder' either through incorporating a radioactive isotope or fluorescent label into one of the nucleotides or the primer used in the reaction. A particular drawback with this technology is its dependence on conventional gel electrophoresis, to separate the DNA fragments in order to deduce sequence information, as this is a slow process taking up to nine hours to complete.

WO97/27331 describes methods for determining nucleic acid sequences in which mass spectrometry is used to detect tags from tagged nucleic acid fragments complementary to a selected target nucleic acid molecule. WO97/27331 proposes cleaving tagged fragments by photolysis followed by subsequent mass spectroscopic determination of purified tags. This method suffers from a number of drawbacks, including the need for expensive equipment to perform the photolysis step.

The present invention aims to overcome the drawbacks of the prior art.

SUMMARY OF THE INVENTION

The present invention provides a method for characterising DNA, which comprises:
(i) providing a population of DNA fragments, each fragment having cleavably attached thereto a mass label for identifying a feature of that fragment;
(ii) separating the fragments on the basis of their length;
(iii) cleaving each fragment in a mass spectrometer to release its mass label; and
(iv) determining each mass label by mass spectroscopy to relate the feature of each fragment to the length of the fragment.

By cleaving each fragment within the spectrometer the present invention possesses advantages over the use of cleavage outside the mass spectrometer, for example by chemical or photolytic cleavage. By designing mass labels which cleave within the mass spectrometer the need for expensive laser equipment or an additional cleavage chamber or interface between separating the fragments and determining the mass label to mass spectrometry is avoided. Cleavage in the mass spectrometer may take place using the ionisation process to induce fragmentation of each mass label. This is described in further detail below. For example, each mass label may be cleavably attached to its respective fragment by a linker which is cleavable in the mass spectrometer.

The method of characterising DNA according to the present invention finds particular application in DNA sequencing. In one aspect, the method further comprises:
(a) providing at least one DNA single-stranded template primed with a primer; and
(b) generating the population of DNA fragments from the at least one template, wherein the population comprises at least one series of DNA fragments, the or each series containing all possible lengths of a second strand of DNA complementary to the or each template;
wherein the feature of each fragment determined by each mass label relates to a nucleotide or nucleotide sequence at one end of each fragments so that each nucleotide is related to a position in the template associated with the mass label so as to deduce the sequence of the or each template.

In a preferred arrangement, the step of separating the fragments is effected by capillary electrophoresis. Capillary electrophoresis systems are amenable to microfabrication which avoid many of the problems associated with conventional gel electrophoresis, most notable of which is the time required for separation of bands. In a micro-fabricated capillary, this can be of the order of minutes rather than hours. Further, because the separation medium can be liquid, loading of capillaries can be easily automated.

The present invention can therefore avoid the limiting step in conventional sequencing techniques of resolution of the fragment population generated by the polymerisation in the presence of blocking nucleotides. The polymerase reaction is simple and relatively fast and can be readily performed in parallel. This is advantageous as it increases throughput. The rapidity, in comparison with the iterative approaches described in GB9620769.1 and GB9700760.1, reduces the time available for secondary structure formation in the templates which can impede chemical and biological steps in the sequencing process.

Thus, by removing the slab gel electrophoretic steps of the prior art, the overall speed of cDNA sequencing can be increased significantly by using capillary electrophoresis and mass spectrometry to derive sequence information.

In one arrangement, the series of DNA fragments is provided by contacting the template in the presence of DNA polymerase with a mixture of nucleotides sufficient for hybridising to the template for forming a second strand of DNA complementary to the template, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavably attached to the mass label, which mass label is uniquely resolvable in mass spectrometry for identifying the modified nucleotide, and wherein each fragment is terminated with one of the probes.

In a further arrangement, at least one template is a plurality of templates and the series of DNA fragments is provided by contacting each template in a separate reaction zone in the presence of DNA polymerase with a mixture of nucleotides sufficient for hybridising to the template for forming a second strand of DNA complementary to the template, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavably attached to the mass label, which mass label is uniquely resolvable in mass spectrometry for identifying the modified nucleotide, wherein each fragment is terminated with one of the probes, and wherein each set of mass labels from each set of four probes associated with each reaction zone is different from the other sets of mass labels; and the fragments are pooled before step (ii).

The present invention is a development of earlier patent applications on primer extension sequencing (GB 9620769.1 and GB 9700760.1). The earlier inventions describe methods for sequencing where a template sequence is determined in an iterative process. The processes described in these earlier patents are potentially limited in the read-length achievable by the efficiency of the chemical and biological reactions occuring in each iteration of the process.

The sequencing process of the present invention allows one to sequence large numbers of Sanger ladder populations, generated in parallel, simultaneously in a fully automated process. This invention thus includes a method for automating the preparation of a large number of Sanger sequencing reactions allowing a large number of templates to be sequenced in parallel.

In a preferred arrangement, the primed DNA may be immobilised on a solid phase support such as a bead or the well of a microtitre plate.

The mixture of nucleotides used in the method typically comprises ATP, TTP, CTP and GTP although their analogues may also be used. All four nucleotides are usually required to ensure that they are sufficient for forming a second strand of DNA to hybridise to the template.

Preferably, the modified nucleotides are dideoxy- or deoxynucleotides which may be added in a concentration suitable to ensure random incorporation into the polymerase reaction. In this way, the DNA ladder of fragments may be produced.

The mass labels may be uniquely resolvable in mass spectrometry in the sense that their mass/charge ratio and/or fragmentation patterns characterise each mass label uniquely so that it may be assigned to a corresponding probe and thereby a corresponding modified nucleotide so that the nucleotide present in the target template sequence may be deduced because it hybridises with the modified nucleotide of the probe. For a simple non-multiplexed method for sequencing DNA it is sufficient to have only four probes, each with its respective modified nucleotide. In other words, four separate mass labels would be required in this simple method. In a multiplexing method, however, multiples of four probes are typically required, the mass labels of each group of four being different from one another. Each group of four mass labels must also be different from the other groups of mass labels so that it is clear which mass label is associated with which reaction zone.

The reaction zones of the present invention are typically separate containers and may conveniently be microtitre wells in a microtitre plate.

In one arrangement according to the present invention a single primed DNA single-stranded template is present in each reaction zone. However, it is possible to have up to four different templates in each separate reaction zone although one or two templates are preferred. Where more than one template is used in each reaction zone the same four probes are used. Statistically it is possible still to assign a unique sequence to each template. Preferably, the relative concentrations of each template are known in this method. This is discussed in further detail below.

In a further arrangement, the at least one template is a plurality of templates and the series of DNA fragments is provided by contacting each template in a separate reaction zone in the presence of DNA polymerase with a mixture of nucleotides sufficient for hybridising to the template for forming a second strand of DNA complementary to the template, wherein the mixture further comprises a probe containing only one of the four nucleotides for hybridising to the template, the nucleotide of which probe comprises a modified nucleotide which is capable of polymerising to the second strand of DNA but blocked to prevent further polymerisation thereto, wherein each fragment is terminated with the probe and wherein either the primer or the modified nucleotide of the probe is cleavably attached to the mass label, which mass label is associated with the reaction zone and uniquely resolvable in mass spectrometry from the mass label in the other reaction zones for identifying the modified nucleotide used in the reaction zone; and the fragments are pooled before step (ii).

In accordance with this method each separate reaction zone contains only one of the four possible modified nucleotides attached to a probe to terminate the polymerisation process. Thus, in each individual reaction zone a DNA ladder corresponding to a template sequence terminating in either As, Ts, Gs or Cs would be formed. By repeating the method for each of the four nucleotides in separate reaction zones the full sequence of the template may be deduced. In this method either the probe or the primer may have cleavably attached thereto its corresponding mass label.

In a further arrangement, the at least one template is a plurality of templates and the series of DNA fragments is provided by contacting the plurality of templates in each of four separate reaction zones in the presence of DNA polymerase with a mixture of nucleotides sufficient for hybridising to the template for forming a second strand of DNA complementary to the template, wherein the mixture further comprises a probe containing in each of the reaction zones only one of the four nucleotides for hybridising to the template, the nucleotide of which probe comprises a modified nucleotide which is capable of polymerising to the second strand of DNA but blocked to prevent further polymerization thereto, wherein each fragment is terminated with the probe and wherein the primer is cleavably attached to the mass label, which mass label is associated with the primer and uniquely resolvable in mass spectrometry from the mass labels associated with the other primers used in the reaction zone; and wherein each nucleotide from its corresponding reaction zone is related to its position in the template.

In a further arrangement, the at least one template is four sets of DNA single-stranded templates, each set comprising an identical plurality of DNA single-stranded templates and the series of DNA fragments is provided by contacting each set in a separate reaction zone in the presence of DNA polymerase with a mixture of nucleotides sufficient for hybridising to the templates for forming a second strand of DNA complementary thereto, wherein the mixture further comprises a probe containing in each of the reaction zones only one of the four nucleotides for hybridising to the template, the nucleotide of which probe comprises a modified nucleotide which is capable of polymerising to the second strand of DNA but blocked to prevent further polymerisation thereto, wherein each fragment is terminated with the probe and wherein each of the templates of the four sets is primed with a primer to which the mass label is cleavably attached, which mass label which uniquely resolvable in mass spectrometry from the mass labels corresponding to the other templates and which is relatable to its respective template and its respective reaction zone, wherein the fragments are pooled before step (ii), and each nucleotide from its corresponding reaction zone is related to its position in the template.

The plurality of single-stranded templates may be primed by hybridising to a known sub-sequence common to each of the templates an array of primers each comprising a base sequence containing a common sequence complementary to the known sub-sequence and a variable sequence of common length, usually in the range 2 to 6, preferably in the range 2 to 4, more preferably 3. The array contains all possible sequences of that common length and the mass label cleavably attached to each primer is relatable to the variable sequence. The variable sequence is relatable to the particular template to be sequenced.

In a further arrangement, the at least one template is a plurality of templates and the series of DNA fragments is provided by contacting each set of templates in a separate reaction zone in the presence of DNA polymerase with a mixture of nucleotides sufficient for hybridising to the templates for forming a second strand of DNA complementary thereto, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavably attached to the mass label, which mass label is uniquely resolvable in mass spectrometry for identifying the modified nucleotide, wherein each fragment is terminated with one of the probes, and wherein each set of mass labels from each set of four probes associated with each reaction zone is different from the other sets of mass labels and, before step (ii), the fragments are pooled and the pooled fragments are sorted according to a sub-sequence having a common length of 3 to 5 bases adjacent to the primer to form an array of groups of sorted fragments, wherein each group is spatially separated from the other groups.

In a preferred arrangement, the step of sorting the pooled fragments comprises contacting the fragments with an array of spatially separate oligonucleotides each comprising a base sequence containing a common sequence complementary to the primer sequence of the fragments and a variable sequence of the common length, which array contains all possible variable sequences of the common length. The common length is preferably 4, in which case an array of 256 spatially separate oligonucleotides is required. The array of spatially separate oligonucleotides is conveniently a hybridisation array and may comprise a hybridisation chip.

In an alternative arrangement, the series of DNA fragments is provided by
(i) contacting the template in the presence of DNA polymerase with a mixture of nucleotides sufficient for hybridising to the template for forming a second strand of DNA complementary to the template, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;
(ii) removing unpolymerised nucleotides;
(iii) unblocking the modified nucleotides; and
(iv) contacting the series of templates with an array of oligonucleotide probes, wherein each oligonucleotide probe has a nucleotide sequence of common length 2 to 6, all combinations of sequences are present in the array, and wherein each probe is cleavably attached to the mass label, which mass label is uniquely resolvable in mass spectrometry for identifying the nucleotide sequence.

In accordance with this arrangement, the series of templates forms a DNA ladder to which the oligonucleotide probes may be ligated. This method may be extended in a further arrangement in which the at least one template is a plurality of primed DNA single-stranded templates, each at a unique concentration, and the series of DNA fragments is provided by
(i) contacting the templates in the presence of DNA polymerase with a mixture of nucleotides sufficient for hybridising to the template for forming a second strand of DNA complementary to the templates, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;
(ii) removing unpolymerised nucleotides;
(iii) unblocking the modified nucleotides; and
(iv) contacting the series of templates with an array of oligonucleotide probes, wherein each oligonucleotide probe has a nucleotide sequence of common length 2 to 6, all combinations of sequences are present in the array, and wherein each probe is cleavably attached to the mass label, which mass label is uniquely resolvable in mass spectrometry for identifying the nucleotide sequence.

The nucleotide probes used to extend the DNA ladder hybridised to the series of templates preferably has a sequence of common length 3 to 5, most preferably 4 nucleotides. In this way, 256 sequences would be present in the array.

The mass label to which each probe is cleavably attached in these alternative methods need not be cleaved in a mass spectrometer and can be cleaved outside the mass spectrometer, for example by photocleavage or chemical cleavage.

In a further alternative method, the series of DNA fragments is provided by contacting the template in the presence of DNA ligase with a mixture of oligonucleotides sufficient for hybridising to the template for forming a second strand of DNA complementary to the template, the oligonucleotides each having a common length in the range 2 to 6, wherein the mixture further comprises a set of probes containing all possible oligonucleotides of the common length 1 for hybridising to the templates in which the oligonucleotide of each probe comprises a modified oligonucleotide which is capable of ligating to the second strand of DNA but blocked to prevent further ligation thereto and which is cleavably attached to the mass label, which mass label is uniquely resolvable in mass spectrometry for identifying the modified oligonucleotide, and the series of fragments contains all possible lengths of the second strand of DNA of integer multiples of 1, in which each fragment is terminated with one of the probes.

The at least one template may be a plurality of primed DNA single-stranded templates each at a unique concentration. In this particular embodiment, the series of DNA fragments is provided by contacting the templates in the presence of DNA ligase with a mixture of oligonucleotides sufficient for hybridising to the templates for forming a second strand of DNA complementary to the templates, the oligonucleotides each having a common length in the range 2 to 6, wherein the mixture further comprises a set of probes containing all possible oligonucleotides of the common length 1 for hybridising to the templates in which the oligonucleotide of each probe comprises a modified oligonucleotide which is capable of ligating to the second strand of DNA but blocked to prevent further ligation thereto and which is cleavably attached to the mass label, which mass label is uniquely resolvable in mass spectrometry for identifying the modified oligonucleotide, and the series of fragments contains all possible lengths of the second strand of DNA of integer multiples of 1, in which each fragment is terminated with one of the probes.

L is preferably 3 to 5, most preferably 4, and once again, the mass labels to which the oligonucleotide probes are cleavably attached need not be cleaved within the mass spectrometer and could be cleaved outside, for example by photolysis or chemical cleavage.

In these further alternative arrangements, instead of producing a DNA ladder with a spacing of one base, a DNA ligase is used and a spacing of 2 to 6 bases is used. This is therefore a ligase chain reaction.

In a further aspect the present invention provides a set of nucleotide probes for use in a method of sequencing DNA from a primed DNA single-stranded template, which set of probes contains all four nucleotides for hybridising to the template, wherein the nucleotide of each probe comprises a modified nucleotide which is capable of polymerising to a second strand of DNA complementary to the template but blocked to prevent further polymerisation thereto, which modified nucleotide is cleavably attached to a mass label for identifying the modified nucleotide, and wherein each mass label when released from the probe is uniquely resolvable in relation to every other mass label in the set by mass spectrometry and is relatable to its corresponding modified nucleotide.

The set of probes may comprise a plurality of sub-sets of probes, each sub-set containing all four nucleotides for hybridising to the template.

In a further aspect the present invention provides a set of oligonucleotide primers, each of which comprises a mass label cleavably attached to an oligonucleotide primer base sequence for hybridising to a DNA single-stranded template to form a primed template, wherein each mass label of the set, when released from the primer, is uniquely resolvable in relation to every other mass label in the set by mass spectrometry and is relatable to the oligonucleotide primer base sequence.

The mass label of each probe or primer may be attached to the modified nucleotide or primer by a cleavable linker which may be cleaved under any appropriate cleavage conditions such as photocleavage conditions or chemical cleavage conditions. The mass labelled probes or primers may be made in accordance with any standard methodology including the methodology disclosed in PCT/GB98/00127 of 15 Jan. 1998 filed by the present applicants.

The present invention will be described in further detail by way of example only with reference to the accompanying drawings, in which:

FIG. 15 shows the results of the method of FIGS. 12 to 14.

EXAMPLES

Automated Preparation of Heterogenous Template Populations:

In order to produce a high throughput DNA sequencing technology the automation of the production of the sequencing template is highly desirable. The following is an outline which describes an automated method of producing sequencing templates for using in the present invention.

Figure 1:
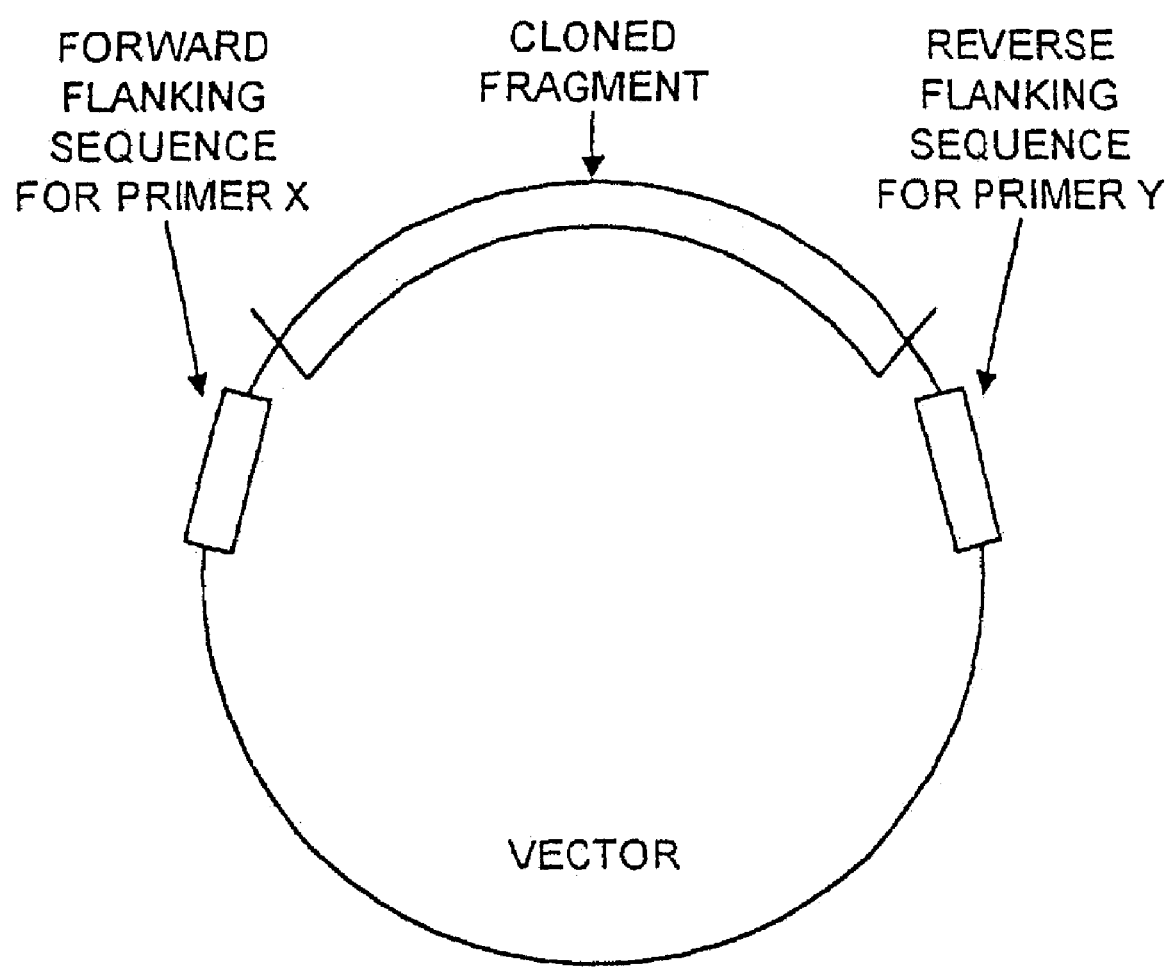
FIG. 1 shows how PCR primers for each cloned fragment may be used in amplification.

For a large scale sequencing project, for example a whole bacterial genome or a full YAC clone, the DNA must first be subcloned into a library. The process of producing a library of this sort can be done in-house or by commercially available services, such as that provided by Clonetech. The DNA is fragmented (e.g. by restriction enzyme digestion or sonification) to sizes in range of a few hundred bases and then subcloned into a cloning vector of choice. Because each fragment in the library is flanked by the same vector sequence a standard set of flanking PCR primers can be used to PCR amplify each each fragment. Using the same PCR primers for each fragment also helps normalise the efficiency of each PCR reaction as primer sequence is one of the most important factors affecting amplification efficiency. (see FIG. 1)

Figure 2:
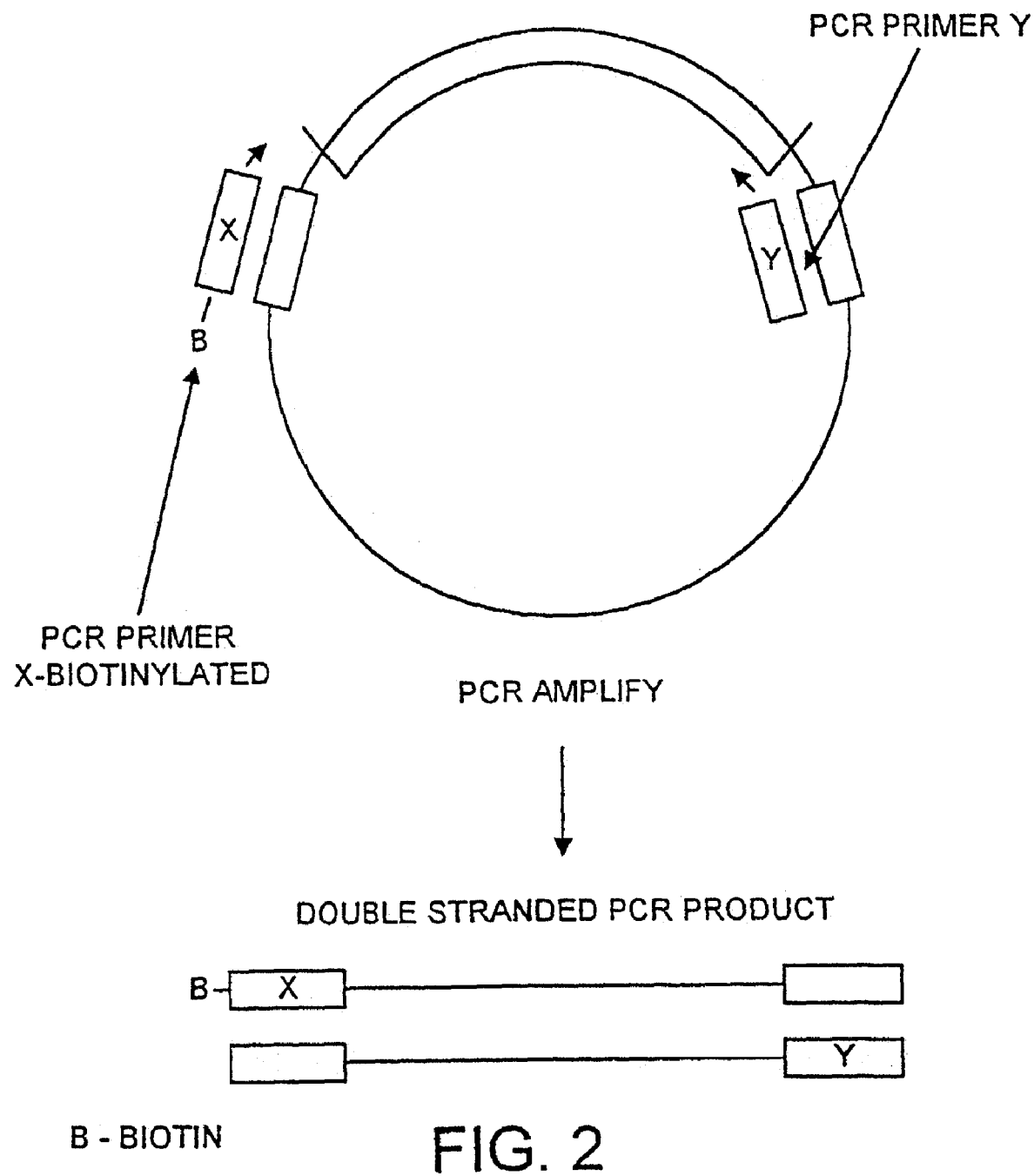
FIG. 2 shows the use of biotinylated PCR primers in fragment amplification.

The library is then transfected into an appropriate bacterial strain and the bacteria plated out onto selective agar plates. Individual colonies (each containing an unique fragment contained within the cloning vector) are then picked by a colony picking robot (which are commercially available). Each picked colony is then spiked into a unique PCR reaction, set up on a microtitre plate for example, and each fragment is PCR amplified using the standard primer set which flank the insert. One of the primers used in this reaction must be biotinylated which will allow the subsequent capture of the amplified fragment. (see FIG. 2)

Following the PCR amplification, a known amount of each of the amplified fragments is then captured on a streptavidin coated surface by its biotinylated primer. By controlling the amount of available streptavidin a specific amount of PCR product can be captured. (This does, however, rely on all the primers being incorporated into the amplification products. This should only require a simple primer titration optimisation experiment as PCR reactions using clones are usually highly efficient.)

Different protocols can be used for this purpose, for example streptavidin coated magnetic beads or streptavidin coated wells of a microtitre plate. When using beads, which will bind 1 pmol of biotin per ul of beads, adding 5 ul of beads and the appropriate buffer to the PCR reaction will capture 5 pmol of the amplified fragment. The use of beads also allows the capture of different quantities of individual amplified fragments. By adding differing amounts of beads to separate amplification reactions prior to pooling them, one can, for example, create a heterogenous population with 1 pmol of fragment 1, 4 pmol of fragment 2, 10 pmol of fragment 3 and so on. Alternatively streptavidin coated wells of a microtitre plate could also be used by transferring each amplification reaction to a unique well of the microtitre plate. Commercially available streptavidin coated plates usually have a maximum binding capacity of between 5 to 20 pmol of biotin. Therefore, of the amount of amplified fragment captured to each well is determined by the binding capacity of that plate.

Figure 3:
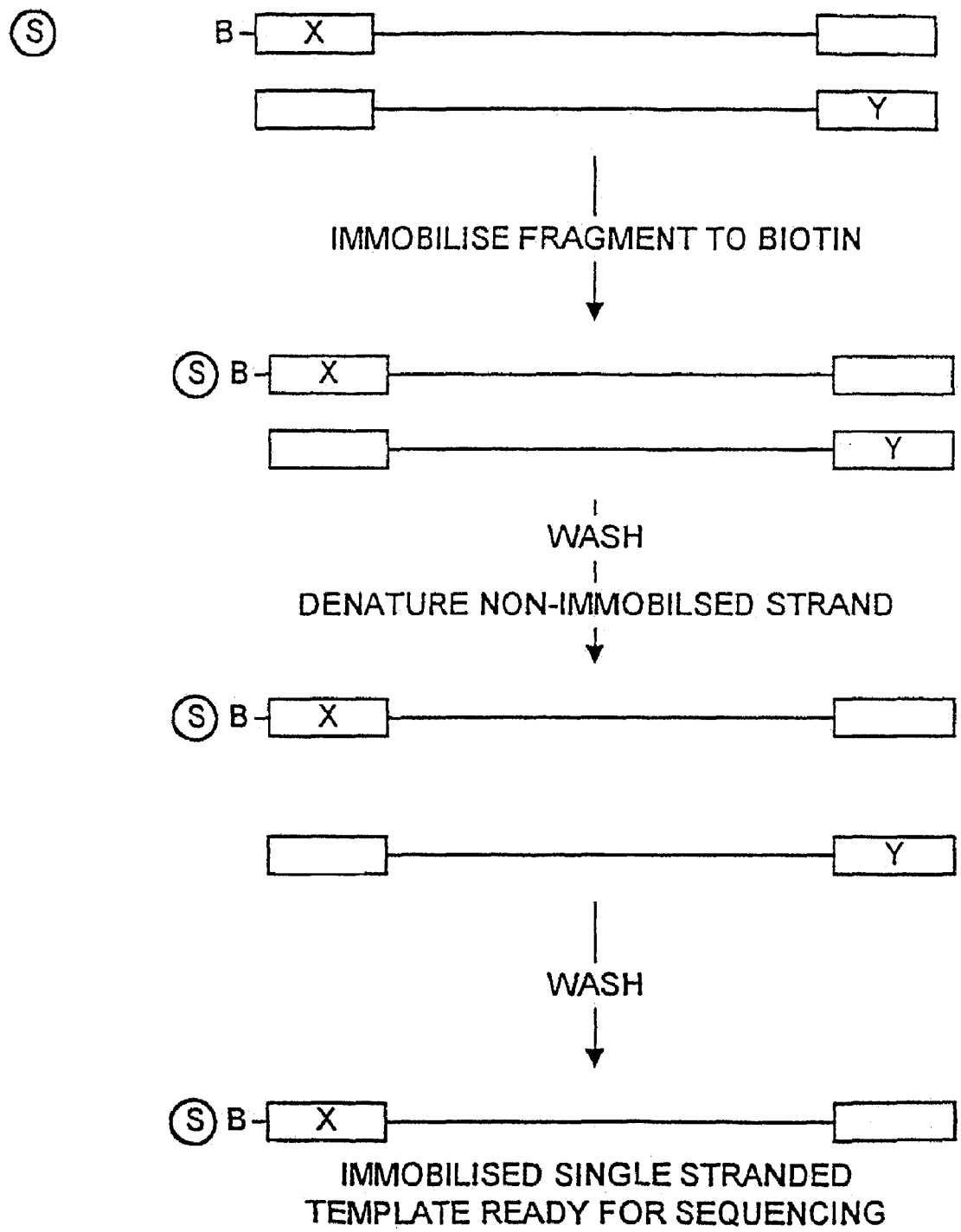
FIG. 3 shows the production of an immobilised single stranded template from double stranded PCR product.

Following capture, excess amplified fragments are then washed away, the double stranded PCR product is denatured with either alkali or heat (or both) (to free the non-biotinylated strand). The non-biotinylated strand is then washed away and this leaves a single stranded template immobilised in the well or tube ready to be used in a sequencing reaction. (see FIG. 3)

DNA Sequencing Using Mass Labelled dNTP's

Figure 4A:
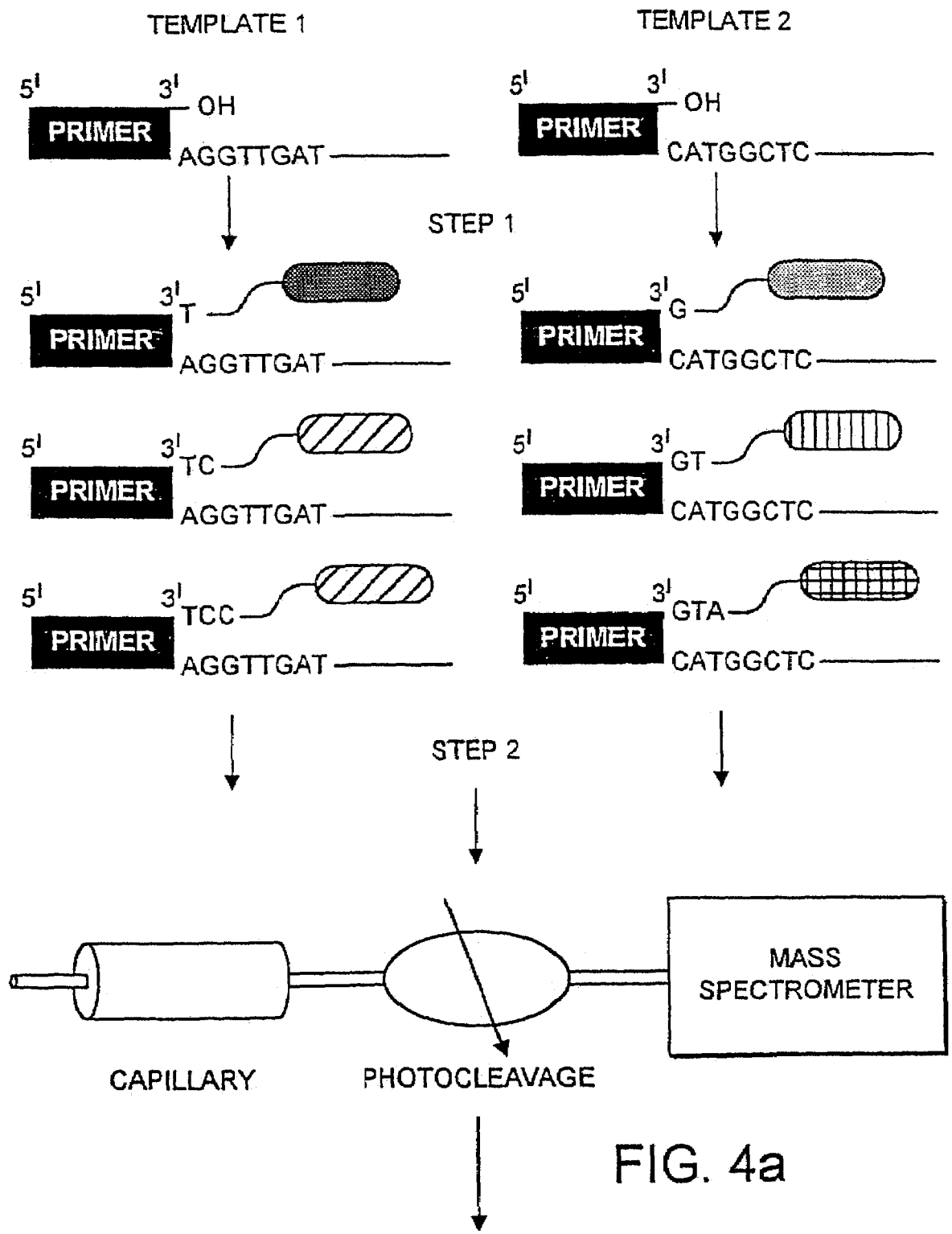
FIGS. 4a and 4b show diagrammatically the method of a preferred embodiment of the present invention.
Figure 4B:
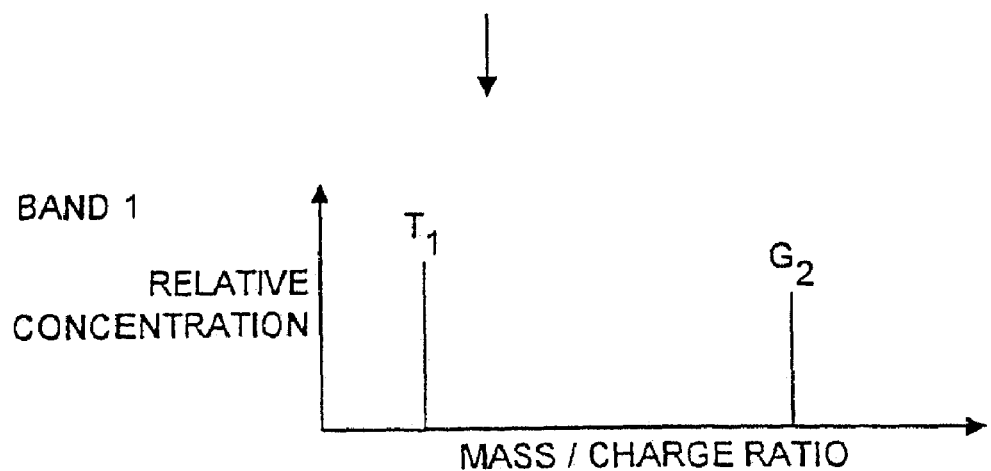
Figure 4B:
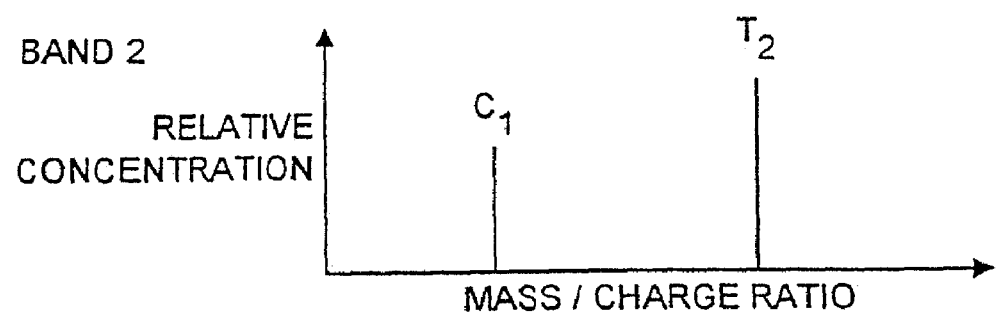
Figure 4B:
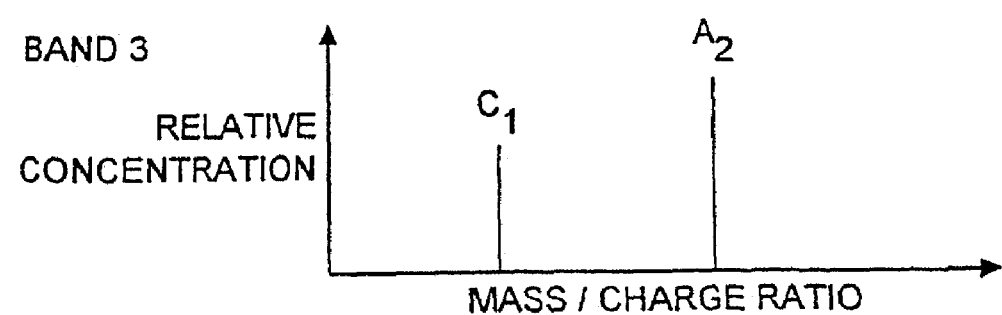

FIGS. 4a and 4b illustrate diagrammaticaly the method of DNA sequencing using mass labelled dNTP's described below.

An immobilised single stranded DNA template is prepared from a PCR product (see above) or by any other appropriate means. Immobilisation can be achieved by biotinylating one of the primers used in the PCR reaction which then allows the subsequent capture of the PCR product to either streptavidin coated beads or wells of a microtitre plate. Following capture, the non-immobilised strand is denatured by alkali or heat (or both) and washed away. The other (non-biotinylated) PCR primer is then annealed to its complementary site on the single stranded PCR product to act as a sequencing primer for a DNA polymerase.

Extension of the sequencing primer is achieved by incubating the template with nucleotide triphosphates, mass labelled deoxynucleotides present at a low concentration and a DNA polymerase (e.g. taq, E. Coli, T7 DNA polymerases or their derivatives—acting in a template specific manner), with appropriate conditions and time. Extension of the primer is blocked in individual templates with a known probability due to the presence of blocking groups on the mass labelled deoxynucleotides (this can be the unique 'mass label' itself) which prevents the 3'OH of the deoxynucleotides reacting with the 5' triphosphates of further nucleotide, thus preventing the addition of any more bases by the polymerase. This is shown in step 1 of FIG. 4a where the Sanger reaction is performed on each template separately using terminating nucleotides that carry mass labels. The unique mass labels are attached to the deoxynucleotides by a cleavable linker group. Cleavage is carried out here by laser light (or possibly by chemical or other means). On cleavage, the mass label is released into solution for analysis.

This embodiment is akin to traditional Sanger sequencing where the blocked nucleotides are present at a low concentration in the presence of ordinary triphosphates. This allows one to generate a Sanger ladder of fragments. In this embodiment the efficiency of photocleavage of the mass labels is not critical to the readlength achievable. One requires just a single sequencing reaction, which means that template is not left standing for long periods of time. Similarly, the potential for photodamage due to repeated photolytic reactions required in the iterative approach of patents GB 9620769.1 and GB9700760.1, is avoided. One can analyse the resultant sequence ladder by capillary electrophoresis followed by direct analysis of mass labels by electrospray mass spectrometry (ESMS).

In step 2 of FIG. 4a, multiple templates are fed into the same capillary electrophoresis electrospray mass spectrometry system. As each band passes through, the mass labels are cleaved by photolysis and injected into an electrospray mass spectrometer for analysis. In a preferred arrangement, no photocleavage apparatus is present and, instead, the mass labels are designed so that, upon entry into the mass spectrometer, the conditions of ionisation are such that the mass labelled fragments cleave and the mass labels are then analysed. As shown in FIG. 4b, the identity of mass labels determines the identity of the nucleotide and the source template from which the sequence is derived.

The use of labelled nucleotides is the preferred format as this avoids certain problems associated with primer labelled sequencing, which is also possible with mass labelling. Polymerase reactions do often terminate prematurely, without the intervention of blocked nucleotides. This is a problem with primer labelled sequencing because the premature termination generates a background of labelled fragments that are terminated incorrectly. Labelling the blocking nucleotides ensures only correctly terminated fragments are labelled so only these are detected by the mass spectrometer. This then permits cycle sequencing where multiple rounds of primer are added to the template. The sequencing reaction is performed using a thermostable polymerase. After each reaction the mixture is heat denatured and more primer is allowed to anneal with the template. The polymerase reaction is repeated when primer template complexes reform. Multiple repetition of this process gives a linear amplification of the signal, enhancing the reliability and quality of the sequence generated.

This invention further avoids problems associated with fluorescence based methods. The large differences in sizes of the commercially available fluorescent labels causes differences in migration of templates of similar length. Since any set of 4 labels used to identify a sequencing reaction can be chosen to be very close in size since a mass spectrometer will comfortably detect differences in mass of one dalton, which should have minimal effect on the relative migration of any given template.

Multiplexing Sanger Ladders:

Given a large number of mass labels one can multiplex a series of Sanger sequencing reactions by labelling the 4 blocking nucleotides with a different set of 4 mass labels in each reaction. Each sequencing reaction would be performed separately and then all the templates would be recombined at the end of the sequencing reactions. The Sanger ladders generated are then all separated together by a single capillary electrophoresis step feeding fragment bands directly into a mass spectrometer for analysis of the labels. Each set of 4 mass labels then correlates to a single source template.

Simultaneous Sequencing:

This invention avoids the need for stringent quantitation. One can however exploit limited quantitation with this invention to compress the number of mass labels needed to sequence a number of templates in parallel. Consider the case where one has 16 labels evenly spread across a clearly distinguishable mass range. One could assign the first four labels to the bases A, C, G, T in that order and use deoxynucleotides labelled in this way to sequence the first template. In a similar manner three other templates can be sequenced. Given that there is a roughly 1 in 16 chance that the same base will appear at the same point in two reactions one can use the same label in two separate reactions, labelling different bases if desired. If two reactions share all 4 labels one can double the number of parallel reactions that can be analysed. If by chance two templates have the same base at a point, clearly only one label will appear for two templates so they clearly share a base. Limited quantitation would be needed to reassign the base calls for each band leaving the capillary electrophoresis system to its source template, but as long as the quantities of templates sharing a set of labels are distinct, this should be relatively simple to do. Furthermore the templates could be sequenced in a single reaction. More templates could be sequenced simultaneously with more stringent quantification of each template. One would need to know in advance how many templates one was sequencing in each reaction and how much of each was present at the start. This may preclude one from using cycle sequencing in which there is a linear amplification of template, if distortion of quantitation cannot be calibrated for.

Separation Techniques:

The separation of a Sanger Ladder by gel electrophoresis imposes limitations on the throughput and accuracy achievable for DNA sequencing. The polymerase reaction used to generate a Sanger ladder is simple and relatively fast and can readily be performed in parallel or even multiplexed in the same reaction. Various novel sequencing methods have been developed that are compatible with PCR and hence exploit automation using 96 well plate robotics and thermocyclers.

Gel electrophoresis works on the simple principle that a charged molecule placed between two electrodes will migrate towards the electrode with the opposite charge to its own. The larger the molecule is for a given charge the more slowly it will migrate towards the relevant electrode. Nucleic acids are poly-ions, carrying approximately one charge per nucleotide in the molecule. This means that nucleic acids of any size migrate at approximately the same rate ignoring frictional forces from the separation medium. The effect of frictional forces is related to the size of the molecule or in the case of nucleic acids, the length of the molecule. This means that nucleic acids are effectively separated by length. The role of the gel matrix is to provide frictional force to impede migration. The speed of separation is proportional to the size of the electric field between the two electrodes. This means that increasing the size of the electric field will reduce separation times, however the electrical resistance of the separation medium means that heat is generated as a result of the electric field and the heat increases with the electric field. The higher temperatures increase the kinetic energy imparted to the analyte leading to greater diffusion and band broadening. This reduces the resolution of the separation. Gels can be cooled but heat dissipation from a slab gel is limited by its surface/volume ratio which is essentially a function of the thickness of the gel. Thinner gels dissipate heat better but there is an additional effect of increased resistance. This means that in slab gel techniques using gels of 200 to 400 μm thickness heating becomes severe if the electric field strength is greater than 50 V/cm. Replacement of the slab gel electrophoretic steps is the most attractive target in view to increasing the overall speed of DNA sequencing.

Capillary electrophoresis offers significant advantages over gel electrophoresis as a separation technology. Various approaches to capillary electrophoresis exist but for nucleic acid separations capillary gel electrophoresis is often used. This technique is essentially gel electrophoresis in a narrow tube. The use of a capillary gives an improved surface/volume ratio which results in much better thermal dissipation properties. This allows much higher electric fields to be used to separate nucleic acids greatly increasing the speed of separations. Typically capillaries are 50 to 75 μm wide, 24 to 100 cm long and electric fields up to 400 v/cm can be used although lower fields are used routinely. Increased separation speeds also improve the resolution of the separation as there is less time for diffusion effects to take place and so there is less band broadening. Improved resolution permits greater read lengths, increasing throughput further. The introduction of flowable polymers has meant that time consuming and technically demanding steps of gel preparation associated with slab gel electrophoresis can be avoided and capillaries can be prepared by injection of the sieving matrix. This improves the reproducibility of separations and the injection of polymers is a process which is readily automated.

Multiplexing Sequencing Reactions:

Primer labelled sequencing is also possible with mass labelling which has certain advantages over nucleotide labelled sequencing. Consider the situation where one has a number of templates each with distinct primer sequences. One can label each unique primer with a unique mass label. The template mixture can be divided into four reactions in which only one of each of the four terminating dideoxynucleotides is present. Each template is primed with its uniquely labelled primer. After performing each of the four Sanger reactions, one can resolve each ladder by capillary electrophoresis mass spectrometry. Each band that elutes from the capillary electrophoresis column that contains a-terminated fragment can be related back to its source template by the label linked to its primer. In this way a large number of templates can be sequenced simultaneously in the same reaction.

For each template with a unique primer sequence, one could choose to label the unique primer with a different label in each of the four reactions to identify which terminating nucleotide is present. This would allow one to pool the four individual base sequencing reactions and analyse them simultaneously. This has the advantage that all four reactions are analysed under identical conditions which should avoid ambiguities that might arise when analysing the four reactions separately due to variations in conditions in each analysis.

The advantage of labelling nucleotides in order to detect only correctly terminated nucleotides is lost by labelling the primer. This advantage could be conferred to primer labelling by modifying the terminating nucleotides to carry a marker to allow correctly terminated fragments to be retained for example by affinity to a column. A plausible modification would be addition of (biotimamido)pentylamine to the terminating nucleotides which would allow reversible binding to avidin. For normal sanger sequencing where only one template is analysed at a time this is probably not worthwhile whereas for reactions where many templates are sequenced simultaneously the additional cost of the separation would be tolerable for the improved quality of the sequence data that would be generated.

Preparation of Templates with Unique Primers:

In order to permit simultaneous sequencing reactions with mass labels one requires that each template be identifiable with a uniquely labelled sequencing primer. One could conceivably engineer a family of cloning vectors that bear different primer sequences flanking the integration site for the exogenous DNA to be sequenced. Each sequencing reaction would be performed on a group of templates where only one template derived from each vector type is present so that all the templates in a reaction bear unique primers. Further details of these methods are described in copending International Patent Application filed on 13 Jul. 1998 by the present applicants [PWF Ref: 87847].

Adaptors to Introduce Primers to Restriction Fragments:

One can, however, exploit the ability to sequence numerous templates simultaneously to cut out sub-cloning steps in a sequencing project. Consider a large DNA fragment such as a mitochondrial genome or a cosmid. One can cleave such a large molecule with a frequently cutting restriction enzyme to generate fragments of the order of a few hundred bases in length. If one uses a restriction endonuclease like Sau3A1 one is left with fragments with a known sticky end to which one can ligate adaptors bearing a known primer sequence.

Figure 5:
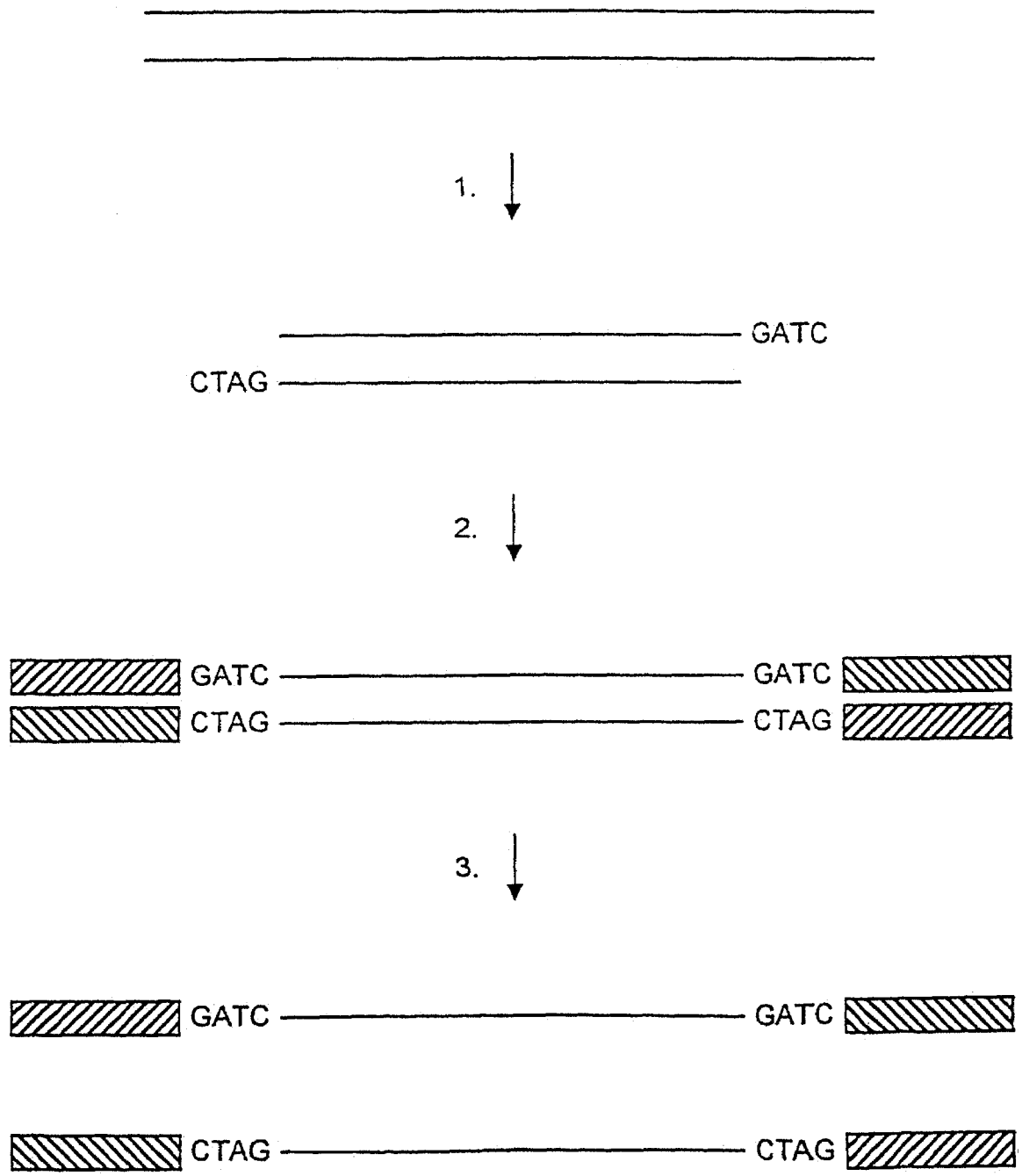
FIGS. 5 to 10 show diagrammatically the methods of further preferred embodiments of the present invention.
Figure 6:
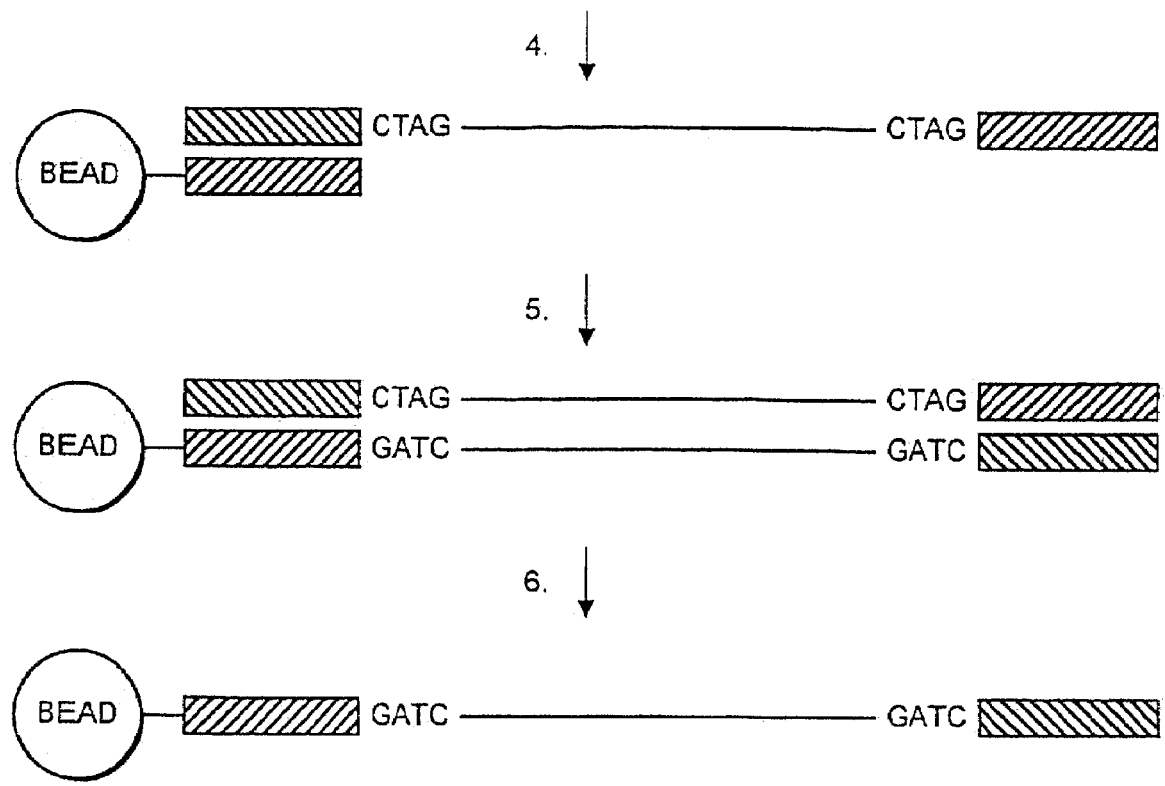
Figure 7:
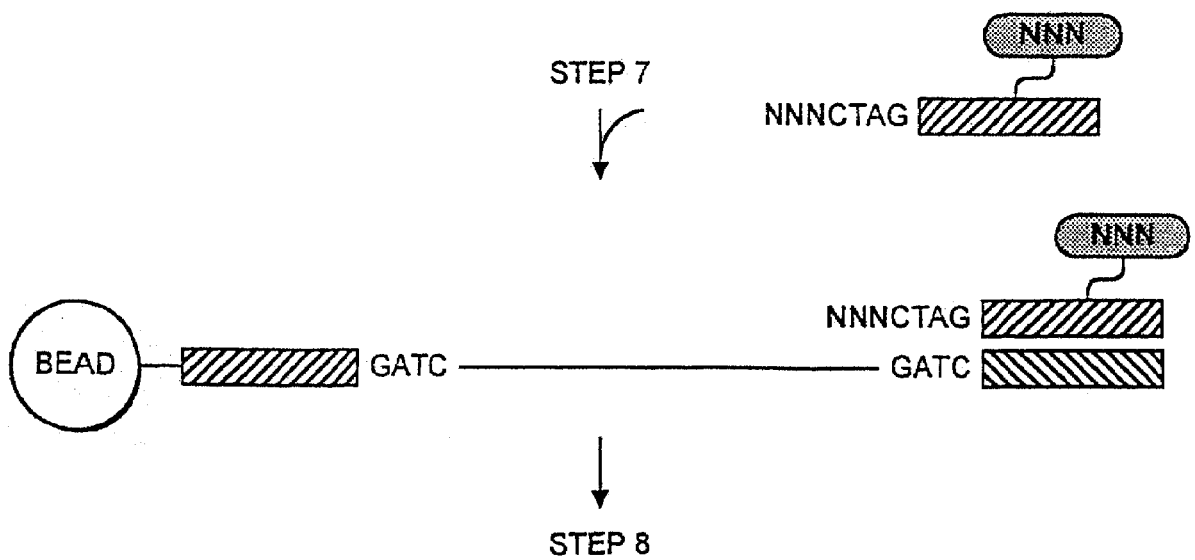

This approach is shown diagrammatically in FIG. 5. In step 1, a genomic DNA clone is treated with a frequent cutting restriction endonuclease such as Sau3A1. In step 2, adapters are ligated to the restriction fragments bearing specific primer sequences. All fragments are dealt with simultaneously although, for simplicity, only one is shown in the Figure. In step 3, the DNA is denatured after an optional amplification step and optional cleaning up steps to remove unligated adapters and restriction enzymes. FIG. 6 shows a continuation of this process in which the single-stranded DNA is captured using an immobilised primer complementary to the adapter primer sequence. In step 5, the immobilised primer and appropriate polymerase is used to generate a complementary strand. In step 6, the free strand is melted off and washed away or recaptured onto immobilised primer to generate further copies of template, if desired. In FIG. 7, mass labelled primers are added at step 7. The mass label identifies bases overlapping into unknown sequence. By step 8, the majority of DNA molecules in a small population should be uniquely primed in this way and a primed population can thus be used for extension in a Sanger sequencing or cycle sequencing reaction.

Figure 8:
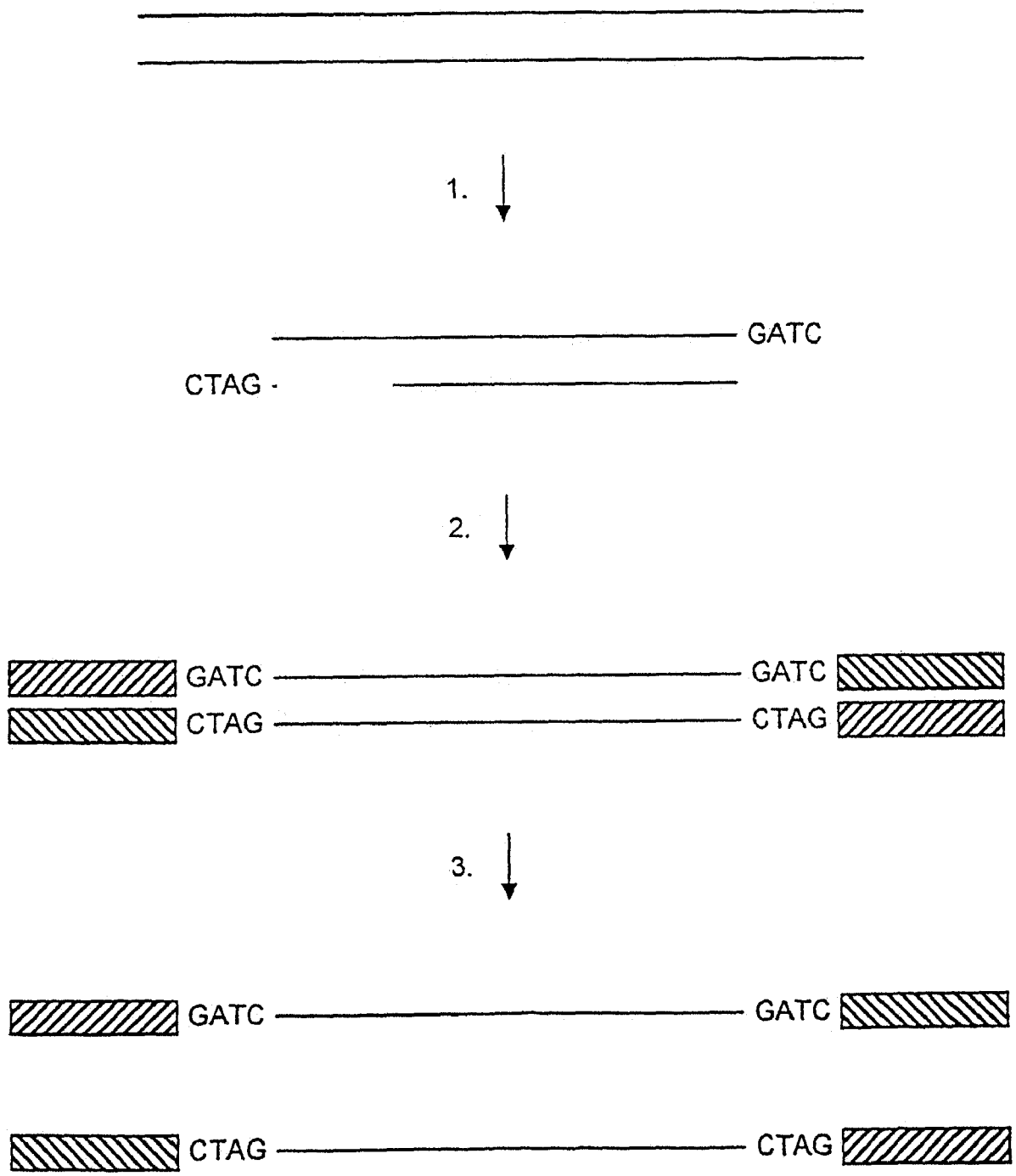
Figure 9:
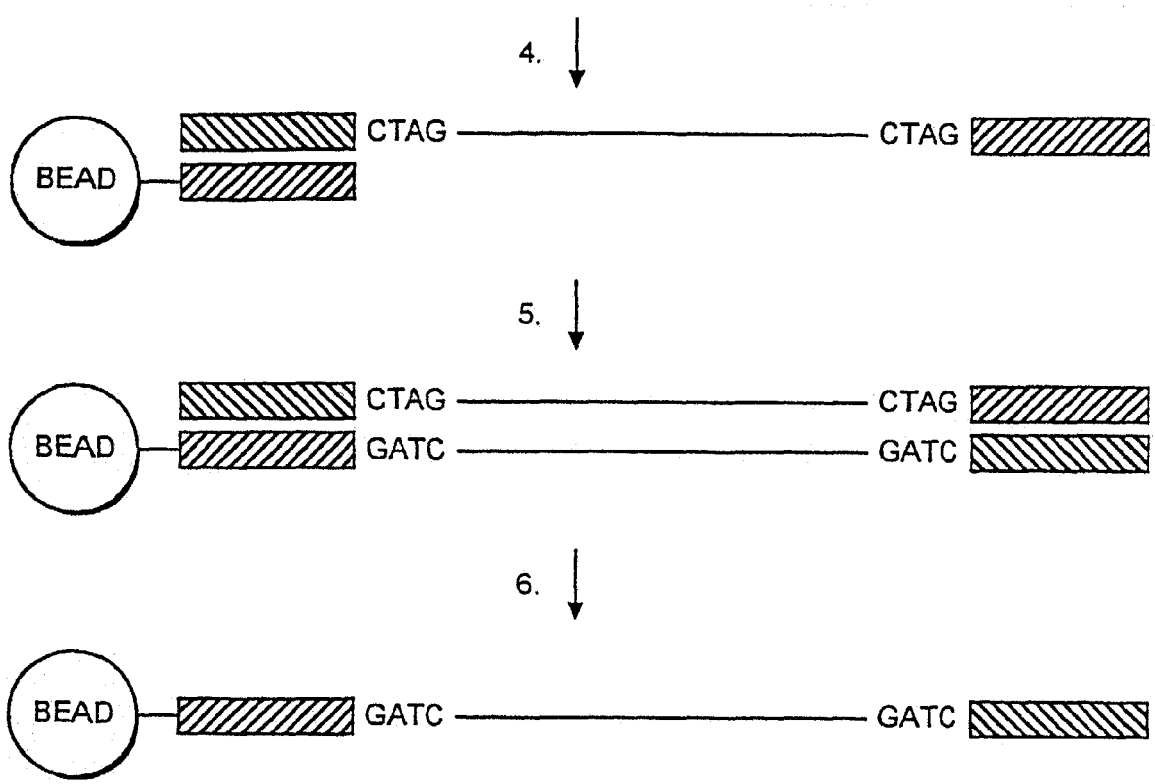
Figure 10:
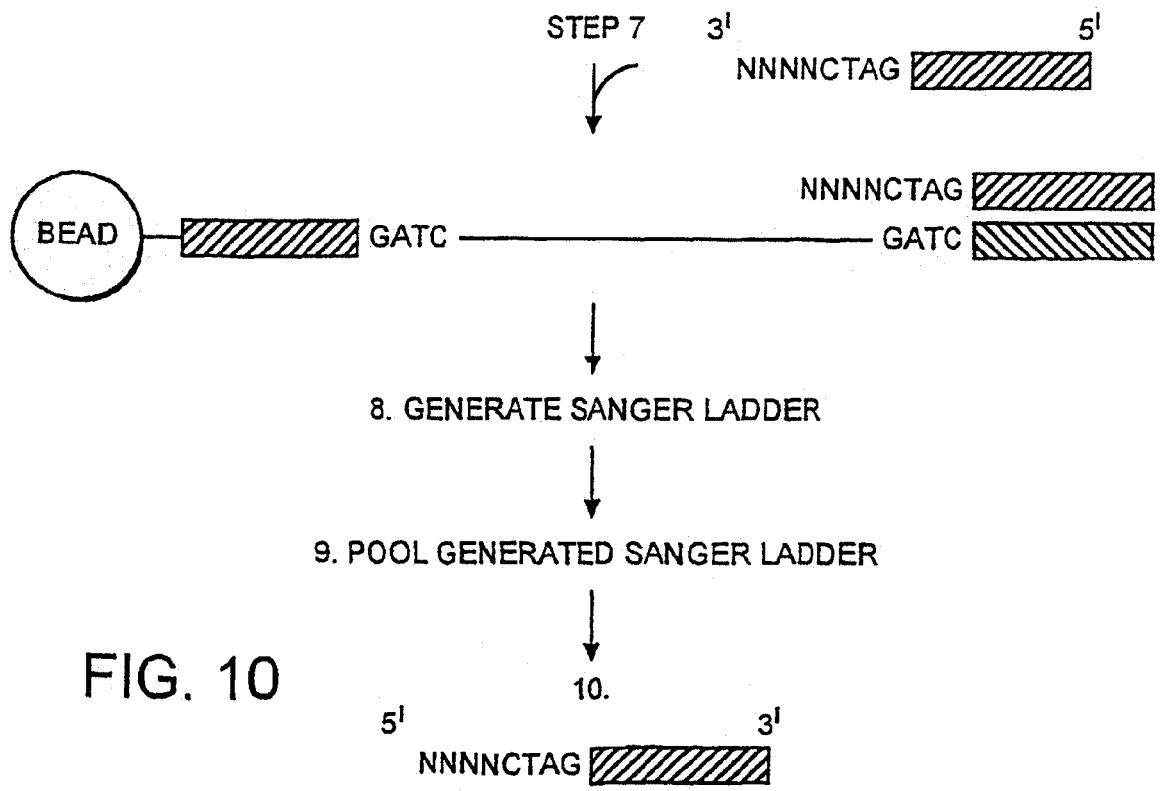

Similar steps are shown in FIGS. 8 to 10.

The majority of properly restricted fragments should as a result bear an adaptor at each of their termini. This permits amplification of the adaptored restriction fragments at this stage if that is desired. After adaptoring and any amplification, one denatures the adaptored fragments and hybridises these fragments to a 'capture' primer. The capture primer could be biotinylated and presented to the adaptored fragments free in solution, after which captured fragments can be immobilised onto a solid phase support derivitised with avidin. Alternatively the primer could be immobilised onto a solid phase support prior to exposure to the adaptored restriction fragments. At this stage one would divide one's template into four separate pools in order to sequence each pool with a different terminating nucleotide.

The captured fragments are made double stranded at this stage by reaction with a polymerase. This means that immobilised copies of all sequences should be present. The hybridised strand can be melted off at this stage and be disposed of if that is desired. An immobilised complementary strand is retained. One can also amplify the sequence present at this stage by further hybridisation with capture primer.

After denaturing free DNA from the immobilised copies of the template and disposing of free DNA, one can add a series of 'sequencing' primers to the reaction. These primers bear the primer sequence in the adaptor and the restriction site by which the adaptors were originally ligated to the DNA and an additional overlap of a predetermined number of bases. If one has 64 labels available the overlap can be 3 bases. Each of the possible 3 base overlaps can be identified by a unique mass label. Given a population of the order of 50 to 60 templates one would expect the majority to have a different 3-mer adjacent to the ligated primer. Thus the majority of templates will be expected to hybridise to a distinct primer. Any template that bears a 3-mer immediately adjacent to the adaptor that is the same as that on another template would only be resolvable if one is able to determine by the quantity of each template which template to assign a base call to.

With the majority of templates primed with a unique primer one can add polymerase, nucleotide triphosphates and one of the four blocking nucleotides to each reaction and can generate Sanger ladders (FIG. 10, step 8). If a thermostable polymerase is used, then the ladders can be denatured at the end of each cycle and fresh primers can be added. If cycle sequencing is used then one would almost certainly want some means to select for properly terminated fragments since cycle sequencing not only amplifies the number of properly terminated fragments but also the number of improperly terminated fragments.

The sanger ladders from each of the four sequencing reactions are then preferrably pooled (FIG. 10, step 9) and analysed together by capillary electrophoresis mass spectrometry so as to avoid any ambiguities in assigning bases due to experimental differences. Each pool of templates would thus have to have its primers labelled with a unique set of mass labels. Thus a total of 256 mass labels would be required. Each primer thus has four labels, one for each terminator reaction. The labels assigned to each primer should be close in mass and size to minimise differences in migration between each termination reaction.

Multiplexing with Nucleotide Labelled Reactions:

A further embodiment of this invention is multiplexing multiple templates in reactions with labelled nucleotides.

Consider a reaction in which unmodified ATP, CTP, GTP and TTP are present with the four corresponding uniquely mass labelled terminating nucleotides. One can generate Sanger ladders for a number of templates simultaneously in the same reaction vessel. If these different templates share a sequencing primer, they can be subsequently sorted into separate groups prior to separation on the basis of the sequence immediately adjacent to the primer. One could separate the fragments onto a hybridisation array where the array bears a sequence complementary to the sequencing primer at all points and an additional predetermined number of bases, N, such that each location on the array bears just one of the possible N base sequences. This means if N is 4 there would be 256 discrete locations on the array. It is expected that a group of templates would in most cases have distinct sequences immediately adjacent to the primer.

This would be an expensive exercise for sorting templates from just one reaction vessel. With a large number of mass labels, however, one can have distinct sets of 4 mass labels identifying blocking nucleotides in a large number of reactions. Thus multiple templates can be added to different reaction vessels, preferably different templates to each reaction vessel. After generating Sanger ladders in each vessel, the reactions can be pooled and the templates from each reaction can be sorted simultaneously. One would expect the majority of ladders of each template from each reaction to segregate to discrete locations on an array and that each location on the array would receive template ladders from a number of distinct reactions.

Having sorted ladders to discrete locations on an array one needs to separate the ladders from each location and identify the mass labels that terminate each set of fragments of each length. How one does this would depend on the array used.

Practically speaking, a hybridisation array could comprise an array of wells on microtitre plates, for example, such that each well contains a single immobilised oligonucleotide that is a member of the array. In this situation a sample of the pooled reactions is added to each well and allowed to hybridise to the immobilised oligonucleotide present in the well. After a predetermined time the unhybridised DNA is washed away. The hybridised DNA can then be melted off the capture oligonucleotide and loaded into a capillary electrophoresis mass spectrometer.

Equally the array could be synthesised combinatorially on a glass "chip" according to the methodology of Southern or that of Affymetrix. One could hybridise the pooled sanger ladders to the chip and wash away unhybridised material. If the probes of the array are immobilised with a linker containing a photo-cleavable group, ladders from discrete locations on the array could be released into solution by application of laser light to the desired location on the array. The solution phase ladders can again be simply loaded into a capillary electrophoresis mass spectrometer.

Again, the advantage of multiplexing and sorting templates is the ability to avoid a number of subcloning steps in a large scale sequencing project. One would prepare template as described above for primer labelled multiplexing but at the stage when sequencing primer is added, the primers used would not be mass labelled. The blocking nucleotides in each reaction would be labelled instead.

Features of Mass labels:

To acheive the required behaviour from a mass label, certain chemical properties are desirable. These are represented in particular molecular groups or moieties that can be incorporated into mass labels in a number of ways.

For the purposes of generating mass labels, favoured labels require a cleavable bond in the linker and fragmentation resistant bonds in the mass label.

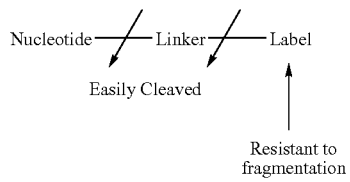

For optimal performance using present techniques a mass/charge ratio of up to 2000 to 3000 units is the optimal range for such labels as this corresponds to the range over which singly charged entities can be reliably detected with greatest sensitivity, however labels of mass less than 100 to 200 daltons are not ideal as the low mass end of the spectrum tends to be populated by solvent molecules, small molecule impurities, multiple ionisation peaks and fragmentation peaks.

To permit detection one requires labels that have a net charge, but are preferrably not multiply ionisable, i.e. they have a fixed single charge. Furthermore they should should be resistant to fragmentation. This ensures that each peak in the mass/charge spectrum corresponds to a single label and simplifies the analysis of the data. Furthermore this reduces any ambiguity in the determination of the quantity of the label, which is very important for some of the applications for which this invention has been developed.

Various functionalities exist which carry or can carry positive charges for positive ion mass spectrometry. These include but are not limited to amines particularly tertiary amines and quaternary amines. Quaternary ammonium groups carry a single positive charge and do not require ionisation. For positive ion spectrometry these allow great sensitivity. Hence preferred positive ion mass labels should carry at least one such group.

Various functionalities are available to carry a negative charge for negative ion mass spectrometry which include but are not limited to carboxylic acids, phosphonates, phosphates, phenolic hydroxyls, sulphonic acids, sulphonilamides, sulphonyl urea, tetrazole and perfluoro alcohol.

Ionisation Techniques:

For many biological mass spectrometry applications so called 'soft' ionisation techniques are used. These allow large molecules such as proteins and nucleic acids to be put into the mass spectrometer in solutions with mild pH and at low concentrations. Two such techniques are ideal for use with this invention; electrospray ionisation and Matrix Assisted Laser Desorption Ionisation (MALDI).

Electrospray Ionisation:

Electrospray ionisation requires that the dilute solution of biomolecule be 'atomised' into the spectrometer, i.e. in a fine spray. The solution is, for example, sprayed from the tip of a needle across an electrostatic field gradient or into a stream of dry nitrogen in an electrostatic field. The mechanism of ionisation is not fully understood but is thought to work broadly as follows. In a stream of nitrogen the solvent is evaporated. With a small droplet, this results in concentration of the biomolecule. Given that most biomolecules have a net charge this increases the electrostatic repulsion of the dissolved protein.

As evaporation continues this repulsion ultimately becomes greater than the surface tension of the droplet and the droplet 'explodes' into smaller droplets. The electrostatic field helps to further overcome the surface tension of the droplets. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber through a pair of electrodes. The potential difference across these electrodes determines whether positive or negative ions pass into the mass analyser and also the energy with which these ions enter the mass spectrometer. This is of significance when considering fragmentation of ions in the mass spectrometer. The more energy imparted to a population of ions the more likely it is that fragmentation will occur. By adjusting the accelerating voltage used to accelerate ions from the ionisation chamber one can control the fragmentation of ions.

Matrix Assisted Laser Desorption Ionisation (MALDI):

MALDI requires that the biomolecule solution be embedded in a large molar excess of an photo-excitable 'matrix'. The application of laser light of the appropriate frequency (266 nm beam for nicotinic acid) results in the excitation of the matrix which in turn leads to excitation and ionisation of the embedded biomolecule. This technique imparts a significant quantity of translational energy to ions, but tends not to induce excessive fragmentation despite this. Accelerating voltages can again be used to control fragmentation with this technique though.

MALDI techniques can be supported in two ways. One can embed mass labelled DNA in a MALDI matrix, where the labels themselves are not specifically excitable by laser or one can construct labels that contain the necessary groups to allow laser energisation. The latter approach means the labels do not need to be embedded in a matrix before performing mass spectrometry. Such groups include nicotinic, sinapinic or cinnamic acid moieties. MALDI based cleavage of labels would probably be most effective with a photocleavable linker as this would avoid a cleavage step prior to performing MALDI mass spectrometry. The various excitable ionisation agents have different excitation frequencies so that a different frequency can be chosen to trigger ionisation from that used to cleave the photolysable linker. These excitable moieties are easily derivitised using standard synthetic techniques in organic chemistry so labels with multiple masses can be constructed in a combinatorial manner.

Fragmentation within the Mass Spectrometer:

Fragmentation is a highly significant feature of mass spectrometry. With respect to this invention it is important to consider how one intends to identify a mass label. At the two extremes one can either design molecules that are highly resistant to fragmentation and identify a label by the appearance of the label's molecular ion in the mass spectrum. One would thus design families of labels to have unique molecular ions. At the other extreme one can design a molecule with a highly characteristic fragmentation pattern that would identify it. In this case one must design families of labels with non-overlapping patterns or with at least one unique fragmentation species for each label by which to identify each label unambiguously. Fragmentation is, however, a property of the molecule and of the ionisation technique used to generate the ion. Different techniques impart differing amounts of energy to the ion and the chemical environment of the ions will vary considerably, thus labels that are appropriate for one mass spectrometry technique may be inappropriate in others. The preferred approach is to design fragmentation resistant molecules, although some fragmentation is inevitable. This means one aims to identify molecules with a single major species, either the molecular ion or a single very highly populated fragment ion.

Determining Bond Stability in the Mass Spectrometer:

In neutral molecules it is reasonably simple to determine whether a molecule is resistant to fragmentation, by consideration of bond strengths. However, when the molecule is ionised, the bond strength may increase or decrease in ways that are difficult to determine a priori. For example, given a bond, X—Y, we can write:

In the equations above, D(A—B) refers to bond energy of the species in parentheses, I(N) refers to the ionisation energy of the species in parentheses and delta-H is the free energy of formation of the species in parentheses. The upshot of the equations above is that in order to predict whether a bond is likely to be stable under a given set of ionisation conditions we need to know the energy of ionisation of the molecule and the energy of ionisation of the neutral fragment that results from fragmentation at the bond in question.

For example, consider the C—N bond in aniline:

$I(NH_2^*)$=11.14 electronvolts (ev) and $I(C_6H_5NH_2)$=7.7ev

∴$I(C_6H_5NH_2)$<$I(NH_2^*)$ by 3.44ev

The alternative cleavage at this bond is:

$I(C_6H_5^*)$=9.35 electronvolts (ev) and $I(C_6H_5NH_2)$=7.7ev

∴$I(C_6H_5NH_2)$<$I(C_6H_5^*)$

This bond is thus not easily broken in the ion. Aniline, if it has sufficient initial energy to fragment, is generally observed to cleave releasing HCN, rather than by cleavage of a C—N bond.

$I(OH^*)$=13ev and $I(C_6H_5OH)$=8.47ev

∴$I(C_6H_5OH)$<$I(OH^*)$

Similarly considerations apply to phenol:

The alternative cleavage at this bond is $I(C_6H_5^*)$=9.35 and $I(C_6H_5OH)$=8.47ev

∴$I(C_6H_5OH)$<$I(C_6H_5^*)$

Thus C—O cleavage is not observed.

Determining the differences in ionisation energies of molecule and neutral fragments is a general working principle which can be used to predict likely ion bond strengths. If the energy added during ionisation is less than the ionic bond strength then ionisation will not be observed. Typical ionic bonds that have good strength include, aryl-O, aryl-N, aryl-S bonds. Generally, aliphatic type bonds become less stable in ionic form. Thus single C—C bonds are weak in the ion but C═C is still strong. Aryl-C═C tends to be strong too for the same reasons as aryl-O, etc. Aryl or Aryl-F bonds are also strong in ionic form which is appealing as fluorocarbons are cheap to manufacture and are chemically inert.

Similar considerations apply to negative ions, except one must use electron affinities in the equations above rather than ionisation energies.

Linkers to Allow Controlled Release of Mass Labels:

Controllable release of mass-labels from their relevant molecule can be be achieved in response to light or chemical triggers or can be achieved within the mass spectrometer through control of fragmentation. Photo-cleavable and chemically cleavable linkers can be easily developed for the applications described. Many are commercially available.

Cleavage of Mass Labels within the Mass Spectrometer:

An alternative to chemical or photolytic cleavage is the use of the ionisation process to induce fragmentation of labels. One can design a linker that is highly labile in the ionisation process such that it will cleave when the molecule to which it is attached is ionised in a mass spectrometer. There are two factors to consider in controlling cleavage: 1) how much excess of energy is deposited on the ion during the ionisation process and 2) whether this excess is sufficient to overcome bond energy in the ion. The excess of energy deposited is strongly determined by the ionisation technique used. The bond energy is obviously determined by the chemical structure of the molecule being analysed.

Fragmentory Linkers:

As discussed above certain groups are particularly resistant to fragmentation, while others such as aliphatic type bonds are reasonably susceptible to cleavage. In order to design a linker that cleaves in a specified location, one might design a molecule that is broadly resistant to fragmentation but that contains a 'weak link', whose fragment ion is stabilised by the surrounding molecule. Certain structural features are observed to stabilise fragments ions when cleavage occurs at certain bonds in a molecule. Linear alkanes are seen to fragment relatively randomly while molecules containing secondary and tertiary alkyl groups are seen to fragment most commonly at the branch points of the molecule due to the increased stability of the secondary and tertiary carbocations. Similarly double bonds stabilise adjacent carbocations through resonance or delocalisation effects. Similar effects are noted in bonds adjacent to aryl-C— groups.

For the purposes of generating a linker for mass labels, one requires a single mass spectrometrically weak bond in the linker and strong ones in the mass label of the sorts described above. A typical weak bond would be:

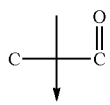

Metastable Ions and Autocleavage of Mass Labels:

Stability is in mass spectrometry is dependant on the ionisation technique used. Broadly speaking an unstable ion is a species that will fragment in the ionisation chamber. Similarly a stable ion will not fragment before reaching the detector. Metastable ions are thus ions that fragment somewhere between the ion source and detector. The temporal distinctions between the classes is somewhat dependant on the configuration of the mass spectrometer used. As mentioned before ionisation techniques have a considerable influence on the degree of fragmentation induced in a population of molecules so what may be a stable ion in electrospray ionisation may be highly unstable under electron ionisation. Furthermore the geometry of the separation stages of the mass spectrometer determines how long an ion exists before detection—ion trap mass spectrometers can obviously store ions for considerable periods of time before detection so molecules which in other geometries reach a detector in high abundance will have time in a trap to fragment.

These factors all have a bearing on the nature of molecule used as a mass label and as a linker. Clearly the design envelope available for such molecules is fairly large.

Induced Cleavage of Labels:

Various analytical techniques have been developed over the years to promote fragmentation of ions for use in structural studies and for unambiguous identification molecules on the basis of fragmentation fingerprints. Most of the ionisation techniques will cause some degree of fragmentation but variations on chemical ionisation techniques can most simply be used to aid fragmentation. Electrospray ionisation can be modified slightly to promote fragmentation. The ionisation chamber can be modified to include a discharge electrode which can be used to ionise the bath gas which in turn will collide with the vaporised sample molecules increasing ionisation and fragmentation of the sample. This technique is termed Atmospheric Pressure Chemical Ionisation (APCI).

A more active approach to fragmentation entails inducing decomposition of molecules such as collision induced decomposition (CID). CID uses tandem mass analyser/spectrometer constructions to separate a stream of ions, then induce collision of the separated Ion stream to promote fragmentation followed by analysis of the resultant ions by a second mass spectrometer. A typical tandem mass geometry comprises two quadrupole mass analysers separated by a collision chamber. This is just a chamber between the two quadrupoles into which a gas can be introduced to allow collision with the ion stream from the first mass analyser. The gas density in the collision chamber must not be too high to permit the collision fragments to pass through, for subsequent separation and analysis by the second quadrupole. Mass labelled molecules could be separated in tandem mass spectrometer so that the first quadrupole separates molecules into streams of a given mass/charge ratio followed by collision which would favour cleavage of labels which can then be analysed in a second mass analyser.

Other techniques are compatible with mass label technologies. A preferred method as discussed earlier is photon induced decomposition. Photon induced decomposition would involve the use of photocleavable mass labels. A typical geometry uses a tandem mass analyser configuration similar to those used in CID, but the collision cell is replaced with a photo-excitation chamber in which the ion stream leaving the first quadrupole is subjected to laser light. High intensity lasers are required to ensure that a significant proportion of a fast moving ion stream interacts with a photon appropriately to induce cleavage. The positioning of the laser is extremely important to ensure exposure of the stream for a significant period of time. Tuning the laser to a specific frequency allows for precise control over the bonds that are induced to cleave. Thus mass labels linked with an appropriate photocleavable linker to their probes can be readily cleaved within the mass spectrometer. The photocleavage stage does not require a tandem geometry, the photocleavage chamber could be within or immediately following the ion source.

A further technique is surface induced decomposition. Surface induced decomposition is another tandem analyser technique that involves generating an ion stream which is passed through the first analyser. This stream is then collided with a solid surface at a glancing angle. The collision fragments can then be analysed by a second separator and detector configuration.

Induced cleavage can be performed in geometries other than tandem analysers. Ion traps mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions.

Mass Label Chemistries:

For any practically or commercially useful system it is important that construction of labels be as simple as possible using as few reagents and processing steps as possible. A combinatorial approach in a which a series of monomeric molecular units are available to be used in multiple cominations with each other would be ideal.

One can synthesise mass labels using standard organic chemistry techniques. Such labels ought to carry a single charge bearing group and should be resistant to fragmentation in the mass spectrometry technique used. Amine derivatives, quaternary ammonium ions or positive sulphur centres are good charge carriers if positive ions mass spectrometry is used. These have extremely good detection properties that generate clean sharp signals. Similarly, negatively charged ions can be used, so molecules with carboxylic acid, sulphonic acid and other moieties are appropriate for negative ion spectrometry. Labels for MALDI mass spectrometry can be generated by derivitising known molecules that are excitable by UV laser light, such as sinapinnic acid or cinnamic acid, of which a number of derivatives are already commercially available. Fragmentation resistant groups are discussed above. For a text on organic chemistry see:

Vogel's "Textbook of Organic Chemistry" 4th Edition, Revised by B. S. Furniss, A. J. Hannaford, V. Rogers, P. W. G. Smith & A. R. Tatchell, Longman, 1978.

Amino Acids:

With a small number of amino acids such as glycine, alanine and leucine, a large number of small peptides with different masses can be generated using standard peptide synthesis techniques well known in the art. With more amino acids many more labels can be synthesised.

E. Atherton and R. C. Sheppard, editors, 'Solid Phase Peptide Synthesis: A Practical Approach', IRL Press, Oxford.

Carbohydrates:

Similarly carbohydrate molecules are useful monomeric units that can be synthesised into heteropolymers OL differing masses but these are not especially amenable to ESMS.

Gait, M. J. editor, 'Oligonucleotide Synthesis: A Practical Approach', IRL Press, Oxford, 1990.

Eckstein, editor, 'Oligonucleotides and Analogues: A Practical Approach', IRL Press, Oxford, 1991.

Other Labelling Chemistries:

Clearly almost any molecule can be tacked onto another as a label. Obviously the properties of such labels in the mass spectrometer will vary. In terms of analysing biomolecules it will be important that the labels be inert, bear a single charge and be resistant to fragmentation.

Linkers for Cleavage within the Mass Spectrometer

Compounds having the formula N—L—M are useful in the present invention where cleavage in the mass spectrometer is desired. N comprises one or more nucleic acid bases and would constitute the nucleotide or oligonucleotide probe or primer. L comprises a linker moiety and M comprises a mass marker optionally having a metal ion-binding moiety. The metal ion-binding moiety is a porphyrin, a crown ether, hexahistidine, or a multi-dentate ligand, preferably a bi-dentate ligand or EDTA. The metal ion-binding moiety may be bound to a monovalent, divalent or trivalent metal ion such as a transition metal ion or a metal ion of Group IA, IIA or IIIA of the periodic table. Preferably, the metal ion is $Ni^{2+}$, $Li^+$, $Na^+$, $K^+$, $Mg^{2+}$, $Ca^{2+}$, $Sr^{2+}$, $Ba^{2+}$, or $Al^{3+}$.

The mass marker may comprise a substituted or unsubstituted polyether which may be a substituted or unsubstituted poly(aryl ether). The polyether may comprise one or more fluorine atom substituents.

L is a group having the formula —$R_1$—Si—$R_2$— in which $R_1$ and $R_2$ are substituents selected such that when the compound reacts with an electron donating moiety, either N or M cleaves from the Si atom in preference to $R_1$ and $R_2$. $R_1$ and $R_2$ are selected such that each has a bond energy to Si greater than the bond energy of N and/or M to Si to ensure that when the compound reacts with an electron donating moiety either N or M cleaves from the Si atom in preference to $R_1$ and $R_2$, and/or $R_1$ and $R_2$ are selected such that their steric bulk is sufficient to ensure that when the compound reacts with an electron donating moiety either N or M cleaves from the Si atom in preference to $R_1$ and $R_2$.

More preferably, $R_1$ and $R_2$ are independently a hydrogen atom, a halogen atom, a substituted or unsubstituted alkyl group or a substituted or unsubstituted aryl group. More preferably, $R_1$ and $R_2$ are each independently fluorine, chlorine, bromine, iodine, methyl, ethyl, propyl, isopropyl, butyl, isobutyl, tert-butyl or phenyl groups. The electron-donating moiety may be a lewis base such as ammonia, a primary secondary or tertiary amine, a compound containing a hydroxy group, an ether or water.

In one example, L is a group having the formula

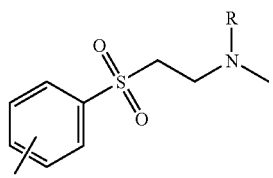

in which R is an electron-withdrawing substituent such as a hydrogen atom, halogen atom, or a substituent comprising a fluorine atom, a chlorine atom, a bromine atom, an iodine atom, a trifluoroacetyl group, or a trifluoromethyl acetate group. L may be attached to N and/or M by a —CO—NH— group, an —NH—CO—NH— group, an —NH—CS—NH— group, a —$CH_2$—NH— group, an —$SO_2$—NH— group, an —NH—$CH_2$—$CH_2$— group, or an —OP(=O)(O)O— group.

Quantification and Mass Spectrometry:

For the most part biochemical and molecular biological assays are quantitative. The mass spectrometer is not a simple device for quantification but, use or appropriate instrumentation can lead to great sensitivity. It must always be remembered that the ion count is not a direct measure of the source molecule quantity, the relationship is a complex function of the molecule's ionisation behaviour. Quantitation is effected by scanning the mass spectrum and counting ions at each mass/charge ratio scanned. The count is integrated to give the total count at each point in the spectrum over a given time. These counts can be related back to the original qunatities of source molecules in a sample. Methods for relating the ion count or current back to the quantity of source molecule vary. External standards are one approach in which the behaviour of the sample molecules is determined prior to measurement of unknown sample. A calibration curve for each sample molecule can be determined by measuring the ion current for serial dilutions of a sample molecule when fed into the instrument configuration being used.

Internal standards are probably the more favoured approach rather than external standards, since an internal standard is subjected to the same experimental conditions as the sample so any experimental vagaries will affect both internal control and sample molecule. To determine the quantity of a sample molecule, an internal standard of a known quantity is added to the sample. The internal standard is chosen to have a similar ionisation behaviour as the molecule being measured. Thus the ratio of sample ion count to standard ion count can be used to determine the quantity of sample as the ratio of qunatities should be the same. Choosing appropriate standards is the main difficulty with this approach. One must find a molecule that is similar but not identical in its mass spectrum. A favourable approach is to synthesise the sample molecule with appropriate isotopes to give a slightly different mass spectrum, for a molecule with the same chemical behaviour. This approach might be less desirable than external standards for use with large numbers of mass labels due to the added expense of finding or synthesising appropriate internal standards but will give better qunatification than external standards. An alternative to isotope labelling is to identify a molecule that has similar but not identical chemical behaviour as the sample in the mass spectrometer. Finding such analogues is difficult and is a significant task for large families of mass labels.

A compromise approach might be appropriate though, since large families of mass labels will ideally be synthesised combinatorially, and will thus be related chemically. A small number of internal controls might be used, where each individual control determines the quantities of a number of mass labels. The precise relationship between internal standard and each mass label might be determined in external calibration experiments to compensate for any differences between them.

The configuration of the instrument is critical to determining the actual ion count itself, particularly the ionisation method and the separation method used. Certain separation methods act as mass filters like the quadrupole which only permits ions with a particular mass charge ratio to pass through at one time. This means that a considerable proportion of sample never reaches the detector. Furthermore most mass spectrometers only detect one part of the mass spectrum at a time. Given that a large proportion of the mass spectrum may be empty or irrelevant but is usually scanned anyway, this means a further large proportion of the sample is wasted. These factors may be a problem in detecting very low abundance ions but these problems can in large part be overcome by correct configuration of the instrumentation.

To ensure better quantification one could attempt to ensure all ions that are generated are detected. Mattauch-Herzog geometry sector instruments permit this but have a number of limitations. Sector instruments are organised into distinct regions, 'sectors', that perform certain functions. In general the ionisation chamber feeds into a free sector which feeds into an 'electric sector'. The electric sector esentially 'focusses' the ion beam which is divergent after leaving the ion source. The electronic sector also ensures the ion stream has the same energy. This step results in the loss of a certain amount of sample. This focussed ion beam then passes through a second free area into a magnetic sector which splits the beam on the basis of its mass charge ratio. The magnetic sector behaves almost like a prism. A photographic plate can be placed in front of the split beam to measure the intensities of the spectrum at all positions. Unfortunately there is a limit on the dynamic range of these sorts of detector and it is messy and cumbersome. Better dynamic range is achievable with electron multiplier arrays, but at a cost of loss in resolution which is limited by how close together the elements of the array can be constructed. With a family of well characterised mass labels one would probably monitor only sufficient peaks to sample all the mass labels unambiguously. In general array detectors would allow one to simultaneously and continuously monitor a number of regions of the mass spectrum simultaneously, which might be applicable for use with well characterised mass label families. The limit on the resolution of closely spaced regions of the spectrum might restrict the number of labels one might use, though, if array detectors are chosen. For 'selected ion monitoring' (SIM) the quadrupole has an advantage over many configurations in that the fields that filter ions can be changed with extreme rapidity allowing a very high sampling rate over a small number of peaks of interest.

Figure 11:
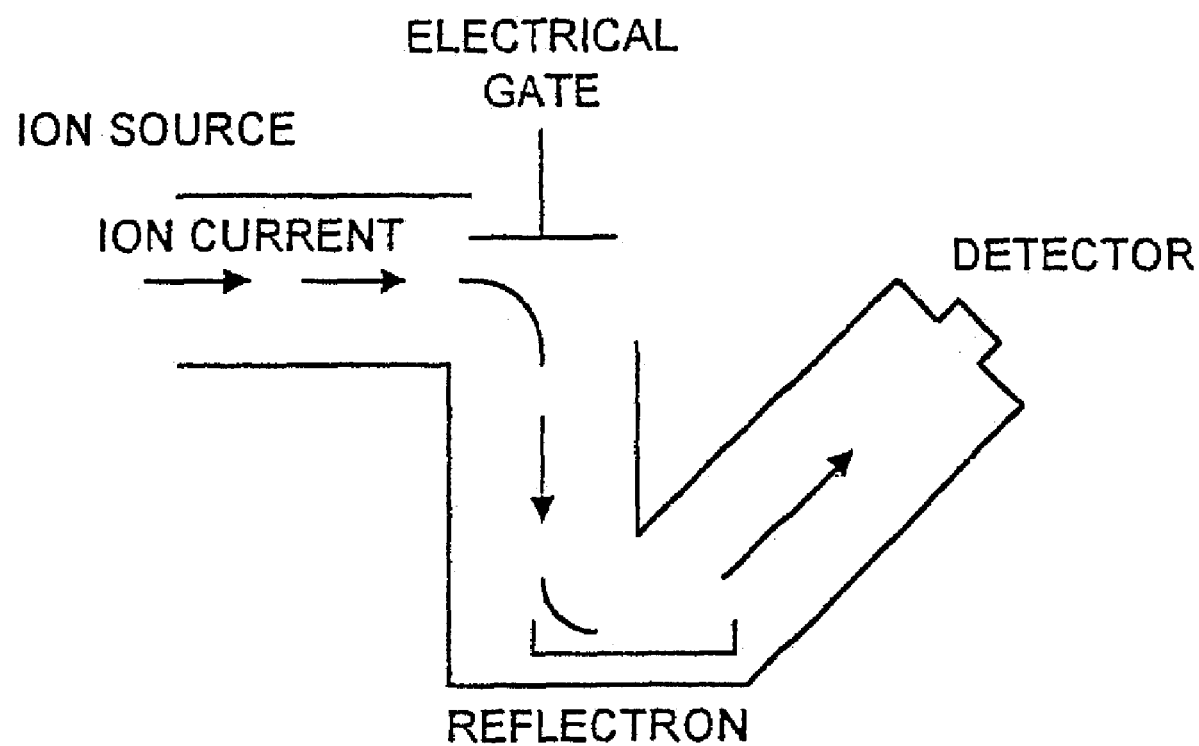
FIG. 11 shows a schemmatic diagram of an orthogonal time of flight mass spectrometer suitable for use in the present invention.

Orthogonal TOF Mass Spectrometry:

An approach that is preferable to array geometries is the orthogonal time of flight mass spectrometer (see FIG. 11). This geometry that allows for very fast sampling of an ion stream followed by almost instantaneous detection of all ion species. The ion current leaving the source, probably an electrospray source for many biological applications, passes an electrode plate perpendicular to the current. This plate is essentially an electrical gate and is used to generate a repulsive potential which deflects the ion current 'orthogonally' into a time of flight mass analyser that uses a reflectron. The reflectron is essentially a series of circular electrodes that generate an increasingly repulsive electromagnetic field that normalises ion energies and reflects the ion stream into a detector. The reflectron is a simple device that greatly increases the resolution of TOF analysers. Ions leaving the ion source will have different energies, faster ions will penetrate the repulsive field further than ions with a lower energy and so will be delayed slightly with respect to the lower energy ions but since they will arrive slightly before the lower energy ions they will enter the TOF at roughly the same time so all the ions of a given mass charge ratio will arrive at the detector at roughly the same time. When the electrical gate is 'closed' to deflect ions into the TOF analyser, the timer is triggered. The flight time of the deflected ions is recorded and this is sufficient to determine their mass/charge ratio. The gate generally only sends a short pulse of ions into the TOF analyser at any one time. Since the arrival of all ions is recorded and since the TOF separation is extremely fast, the entire mass spectrum is measured effectively simultaneously. Furthermore, the gate electrode can sample the ion stream at extremely high frequencies so very little sample is required. For these reasons this geometry is extremely sensitve, to the order of a few femtomoles.

Figure 12:
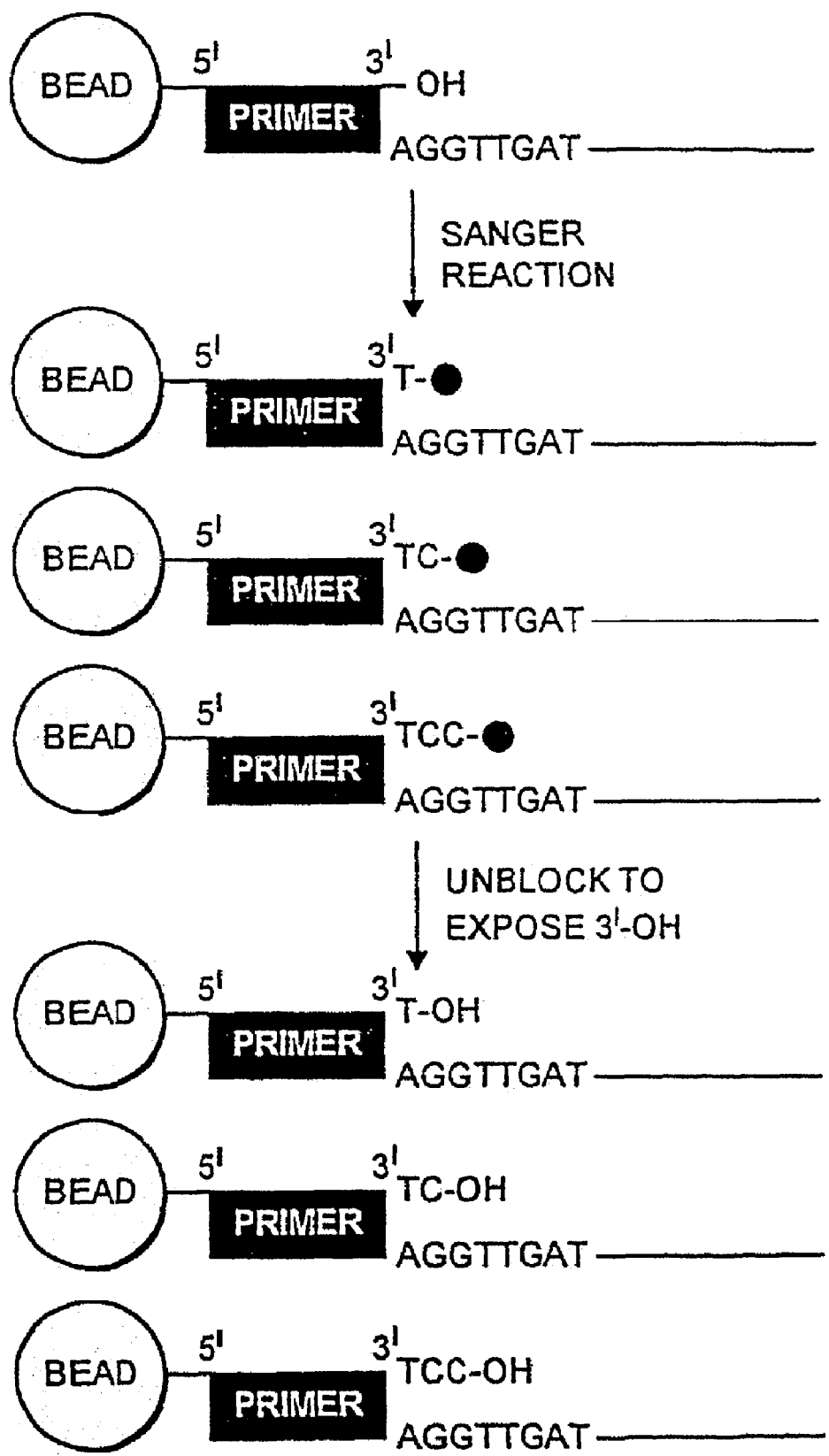
FIGS. 12 to 14 show diagrammatically a method of an alternative embodiment of the present invention using reversably blocked nucleotide probes.

Primer Extension and Parallel Sequencing of Subsets of Nucleic Acid Fragments:

Sequencing a Single Molecule by Ligation of Single Stranded Oligonucleotides to a Sanger-Like Sequence Ladder:

Referring to FIG. 12, consider a population of copies of a single nucleic acid, immobilised at one terminus to a fixed insoluble matrix. This molecule is rendered single stranded, except for a short stretch of double-stranded DNA at the immobilised terminus of the molecule to serve as a primer for the DNA polymerase reaction. This primer sequence could be provided by the adaptor used to immobilise the terminus or could be a PCR primer if the template is an amplified product. Thus far the technology is as taught by (S. Stahl, T. Hultman, A. Olsson, T. Moks, M. Uhlen, 1988, "Solid Phase DNA sequencing using the biotin-avidin system". Nucleic Acids Research. 16, 3025–3038) for solid phase Sanger synthesis. An important feature of this approach is in the blocking nucleotides, which would preferably not be dideoxynucleotides, but rather would be reversibly blocked. This means that after allowing the template to be polymerised in the presence of chain terminating nucleotides, one is left with the expected Sanger ladder of fragments. One can wash away the polymerisation reagents leaving the immobilised Sanger fragments. At this stage the blocking groups are removed to expose a 3' hydroxyl which is amenable to further extension. In the simplest case each terminating base is labelled with a mass label that identifies it uniquely which can be analysed by mass spectrometry as described above, however this does not allow one to really exploit the possiblity of analysing a number of heterogenous sequence templates simultaneously. Thus one would prefer to use a removable blocking group whose identity is not determined and which exposes the 3' —OH of the blocked sequence for further extension.

Figure 13:
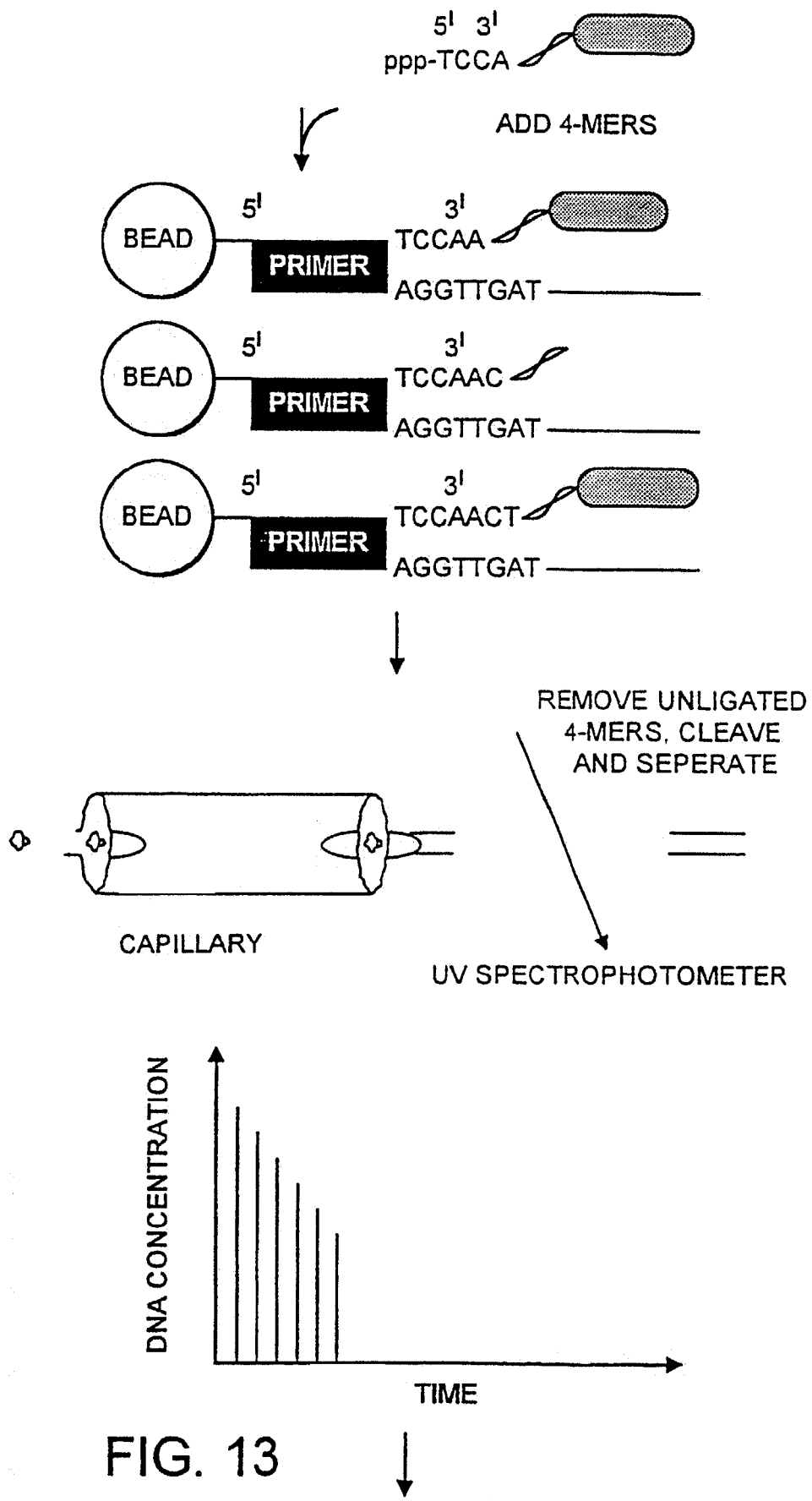

To these exposed termini one can then ligate oligonucleotides of a pre-determined length (N) each bearing a photocleavable mass label that identifies the sequence of the oligonucleotide so that the next N bases of the sequence 3' of the previously nucleotide are identified by a complementary oligonucleotide bearing a label that identifies its sequence. This is shown in FIG. 13. Suitable labelling systems for use with this invention are described herein, as well as in PCT/GB98/00127 of the present applicant. Ligation can be chemical or enzymatic. This stage of the sequencing process will therefore extend each fragment composing the chain terminated population by N bases leaving one with a new ladder of terminated fragments. Mass-labelled oligonucleotides would preferably be added in two sets of 128 such that each member in the first set would have its complement in the other set. This overcomes the problem of cross-hybridisatin between complementary 4-mers.

Figure 14:
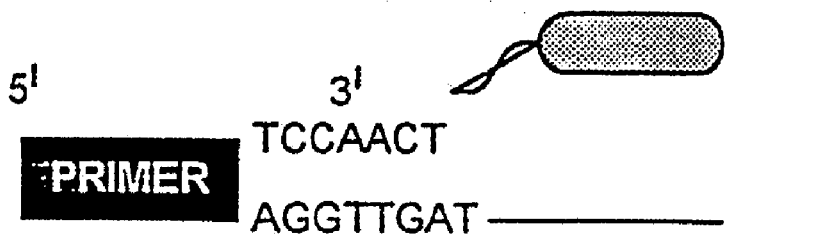
Figure 14:
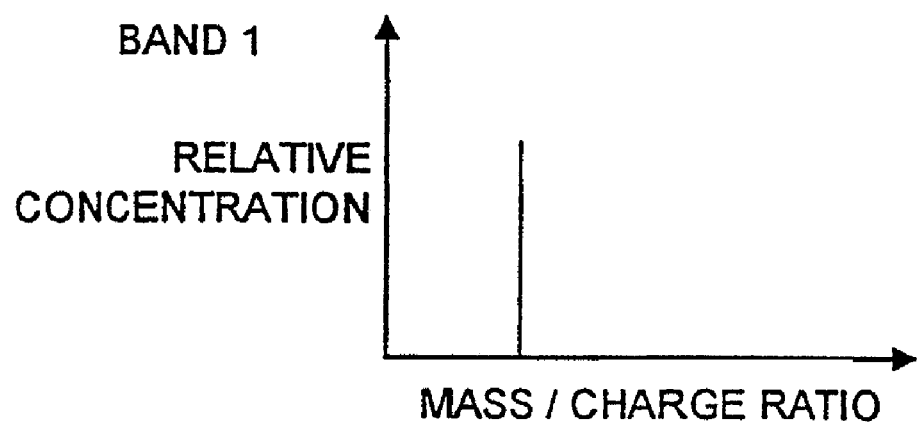
Figure 14:
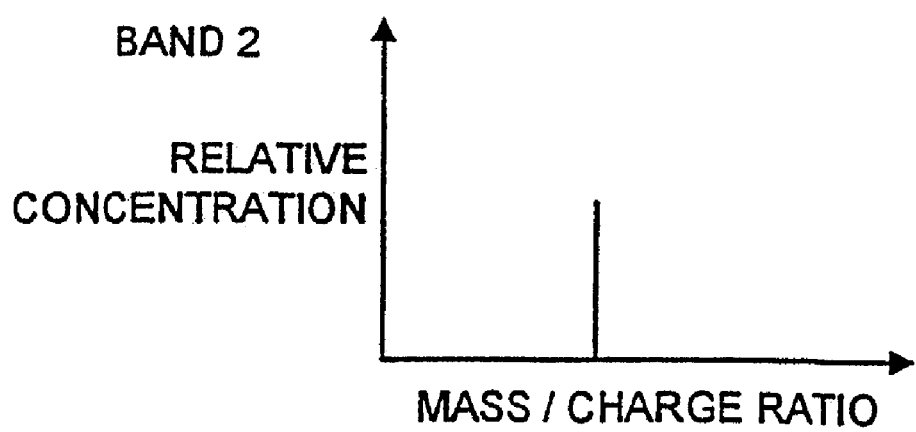
Figure 14:
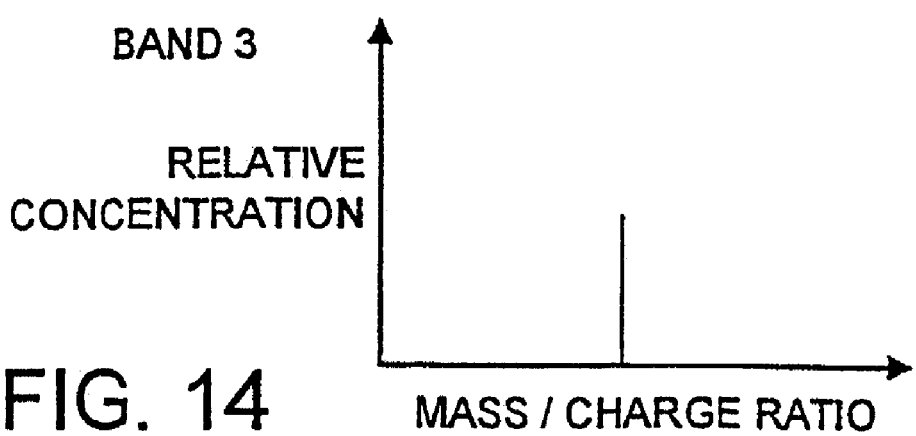
Figure 15:
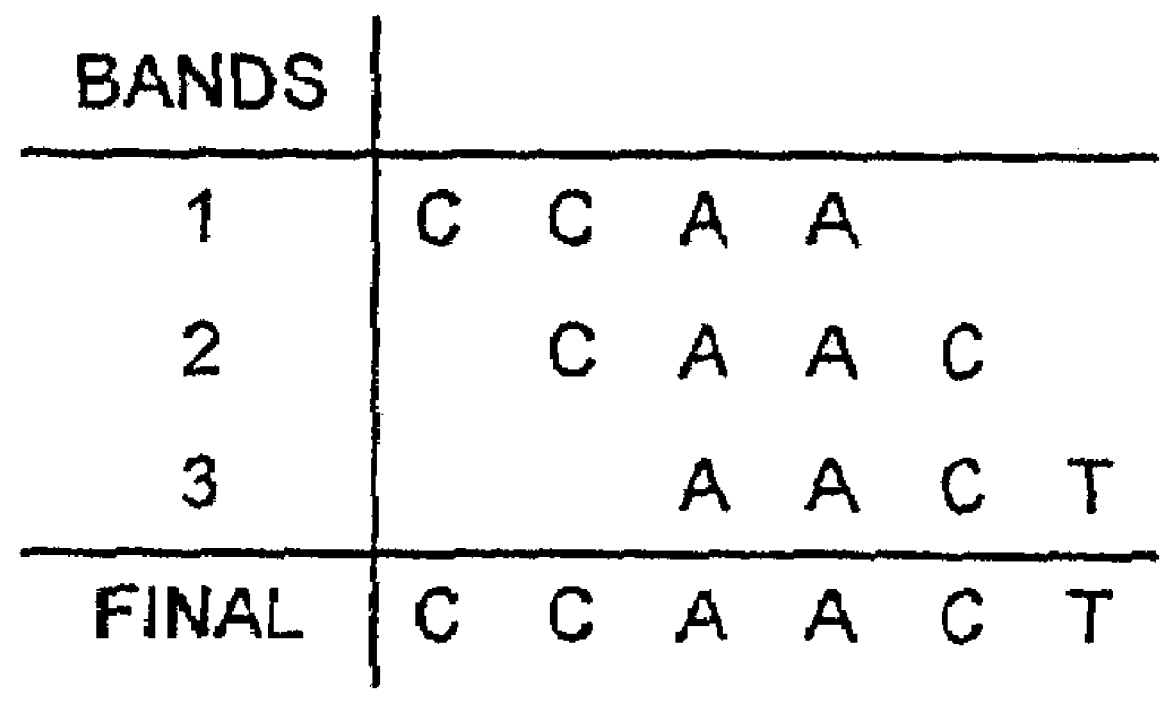

The immobilised matrix can then be washed to remove any unbound oligonucleotides, a water wash would probably be sufficient to disrupt hybridisation. To determine the sequence of the 4 base oligonucleotide that ligated to each Sanger fragment, one need only analyse the label attached to the 3' end of the oligonucleotide. The labelling system for use with this invention is described in PCT/GB98/00127 in which the mass of the label identifies its carrier. Such labels can be made photolabile or cleavable by a specific chemical or biological agent. As detailed in FIG. 14, cleavage of the label will release it into solution in which it can be injected into an electrospray mass spectrometer for analysis, which will determine the sequence of the oligonucleotide and furthermore, its quantity. Sample results are shown in FIG. 15. Prior to cleavage of labels one needs to separate the Sanger ladder into its component fragment lengths. In a mass spectrometry system this stage can be coupled to the sample loading in a LCMS system. Separation into bands can be achieved by capillary zone electrophoresis. This will then pass through a UV spectrometer to determine the quantity of DNA in each band. Following this the sample will then pass through a photocleavage module to release the mass-labels which will then be injected into an electrospray mass spectrometer for analysis of the labels in each band.

In one embodiment one can probe the immobilised Sanger ladder with every one of the possible 256 single-stranded 4 base oligonucleotides. Each of these would carry a unique identifying label corresponding to its known, sequence of 4 bp. In the 5' to 3' format, the label could be attached to the 3' —OH effectively blocking them from further extension, or a separate blocking group can be used and the label can be attached elsewhere in the molecule.

One could use chemical ligation rather than enzymatically catalysed ligation if that is preferred. This may be advantageous as it would permit probes to be synthesised from DNA analogues not accepted by a ligase such as Peptide Nucleic Acid (PNA) or other analogues. PNA is desirable as it has higher affinity for its complementary DNA sequence than DNA probes.

Other advantages may be that chemical ligation would allow the use of electric fields to regulate the stringency of hybridisation of probes electrostatically.

In a preferred embodiment, a photolysable linker would connect the mass label to the 3' —OH which when cleaved would regenerate the 3' —OH with as high an efficiency as possible. The primer has then been extended by 4 known bases and the cycle can be repeated to determine the next 4 bp of sequence. This process can be repeated iteratively until the entire molecule has been sequenced.

An alternative implementation to using photolysable mass labels at the 3' —OH of each 4-mer oligonucleotide would be to cap the 3' —OH with a phosphate group. One could also use dideoxynucleotides or any other appropriate means to block the 3' —OH of the probe molecules. The mass-label could be attached to another part of the molecule from which it can be released independently of the uncapping reaction of the 3' terminus. Uncapping of the 3' terminus can be effected by washing the immobilised DNA with alkaline phosphatase which will readily remove the capping phosphate from the 3' —OH leaving it available for the next cycle of the sequencing process.

Conceivably this system could be implemented with other labelling schemes, but most other labelling schemes do not generate sufficient, unique labels to be practical.

Sequencing a Population of Nucleic Acid Fragments:

The same process can be applied to a heterogeneous population of immobilised nucleic acids allowing them to be analysed in parallel. To be successful when applied to a population of nucleic acids, this method relies on the assumption that statistically 1 out of 256 molecules within the total population will carry each of the possible 4 bp sequences adjacent to each terminated Sanger fragment. If one sub-sorts ones nucleic acid population into manageable subsets of less than 256 fragments, one would expect that almost all will have different sequences following each terminating base in the Sanger ladder so for most purposes one can assume that a hybridisation signal corresponds to a single DNA type. This all assumes that DNA sequences are random sequences of bases which is not strictly true but is a sufficient assumption for the purposes of this invention. Obviously 1 in a 1000 is not a small probability and sequences will often have the same 4-mer at the same point in a Sanger ladder.

However this invention includes algorithms that can resolve to a great extent any possible ambiguities caused by this occurrence.

Reconstructing Sequences of Target Nucleic Acids:

Analysis of the labels in each band of the modified Sanger ladder will generate a matrix of quantities of label corresponding to each possible probe. Shown below is a possible matrix for all probes of 4 base pairs in length:

| Sequence to which label corresponds | Cycle 1 | Cycle 2 | Cycle 3 | Cycle 4 |
|---|---|---|---|---|
| AAAA | 5 | 24 | 13 | 7 |
| AAAC | 10 | 5 | 9 | 13 |
| AAAG | 13 | 9 | 15 | 17 |
| ... | ... | ... | ... | ... |
| TTTG | 7 | 13 | 17 | 10 |
| TTTT | 17 | 10 | 7 | 14 |

To reconstruct the sequences to which these quantities of label correspond, this invention also envisions algorithms for analysing such a data matrix. The algorithm attempts to identify a sequence on the basis of its frequency, i.e. a sequence present at a given frequency will have every subsequence present at the same frequency. The algorithm searches through each column of the matrix and attempts to resolve label quantities, that may be sums of sequence frequencies into atomic quantities such that the same set of atomic quantities appear in all columns. The algorithm acheives this by comparing label quantities in a given column with those in all the other columns. A given atomic quantity that appears in all columns is then assumed to correspond to a unique sequence.

If two sequences have the same n-mer at a particular point in the sequence, these can be resolved by the quantitative nature of this system in that the quantity of a particular n-mer in a particular ligation will be the sum of the quantities of the two sequences that share the n-mer at the same point. These can be largely resolved by comparison of one cycle with previous and subsequent ligation cycles to identify such sums. This is made particularly simple if the sequences that are being analysed have been amplified by PCR such that the sequence in the lowest quantity is present at not less than half the quantity of the sequence with the greatest frequency, that is to say if the frequency range of sequences lies between some quantity N and 2N. This means that any sum of frequencies will be greater than 2N and hence readily detectable.

Notice that if the sequence template is a Sanger Ladder, ligation and identification of 4-mers to such a ladder will provide overlapping 4-mers, thus providing significant redundancy that should provide sufficient information to eliminate most ambiguities that might arise in individual columns of the reconstruction matrix.

Ligase Chain Reaction:

A further embodiment of this invention uses a variant of the Ligase Chain Reaction. A single stranded template is immobilised and then primed at the 3' terminus of the molecule. To this immobilised template is added the 256 possible 4-mers in the presence of a ligase. The 4-mers are phosphorylated at the 5' terminus. For each 4-mer variant a small, pre-determined proportion of the probe is present with its 3' —OH blocked with a photocleavable mass label. The 4-mers will hybridise to the template and the ligase will ligate them. However, for any given copy of the template there will be a distinct probability that an irreversibly blocked 4-mer will be incorporated at a given point, thus preventing further extension.

This will generate a ladder of terminated fragments in a manner that is analogous to the Sanger sequencing reaction. The identity of the terminating 4-mers can be determined by separating the terminated fragments by capillary electrophoresis followed directly by analysis of the photocleaved mass labels by electrospray mass spectrometry.

Here again multiple templates can be analysed simultaneously because of the fact that at any point in the sequence a given 4-mer will occur at a relatively low probability.

This embodiment permits an additional level of multiplexing. This embodiment will give a ladder of fragments where each fragment is N bases longer than the previous fragment where N is the length of the ligation probes used. Capillary electrophoresis will give single base resolution so if the template population is divided into 4 subsets, one can prime each subset with a primer one base longer than the previous primer. This will give 4 populations of fragments resolved from each other by a single base.

Ligation of Sanger Ladders to an Array of DNA Probes and MALDI Detection of Fragments:

A further embodiment of the invention uses immobilised probes rather than mass labelled probes in solution. In this embodiment a Sanger Ladder of fragments is generated as described above. The immobilised fragments are then released from the solid phase substrate and ligated to an array of oligonucleotides bearing all $4^N$ probes of length N at discrete locations on the array surface. The linkers attaching the probes to the array surface would be photocleavable. The array would then be washed and treated with an appropriate exonuclease to trim any single-stranded. DNA remaining. The array would be washed again and a suitable MALDI matrix would be applied to the array. The array would be placed in MALDI-TOF spectrometer and each location on the array surface, corresponding to a specific N-mer probe, would be scanned by a laser, first at a frequency to cleave the linker immobilising the probes and then at the frequency required to excite the matrix used. This will ionise the fragments ligated to the surface at the location scanned. These will be detected by Time Of Flight spectrometry.

For each location on the array one will thus know the sequence of the N bases of 3' of the termination point in each fragment, the mass hence length of the fragments ligated and the quantity of each fragment. This will allow the generation of an equivalent data matrix to that for the capillary electrophoresis mass spectrometry embodiment to be generated.

What is claimed is:

1. A method for characterizing DNA, which comprises:
   (i) providing a population of fragments of said DNA, each fragment having cleavably attached thereto a mass label for identifying a feature of that fragment;
   (ii) separating the fragments on the basis of their length by capillary electrophoresis, thereby determining the length of each fragment;
   (iii) cleaving each fragment in a mass spectrometer by collision to release its mass label; and
   (iv) determining each mass label by mass spectrometry to relate the feature of each fragment to the length of the fragment in order to characterize said DNA.

2. A method according to claim 1, which further comprises the following steps before step (i):
   (a) providing at least one DNA single-stranded template primed with a primer; and
   (b) generating the population of fragments of said DNA from the at least one template, wherein the population comprises at least one series of DNA fragments, the or each series containing all possible lengths of a second strand of DNA complementary to the or each template; wherein the feature of each fragment determined by each mass label relates to a nucleotide or nucleotide sequence at one end of each fragment, so that each nucleotide is related to a position in the template associated with the mass label so as to deduce the sequence of the or each template.

3. A method according to claim 2, wherein the series of DNA fragments is provided by contacting the template in the presence of DNA polymerase with a mixture of nucleotides for hybridising to the template for forming a second strand of DNA complementary to the template, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavably attached to the mass label, which mass label is uniquely resolvable in mass spectrometry for identifying the modified nucleotide, and wherein each fragment is terminated with one of the probes.

4. A method according to claim 2, wherein the at least one template is a plurality of templates and the series of DNA fragments is provided by contacting each template in a separate reaction vessel in the presence of DNA polymerase with a mixture of nucleotides for hybridising to the template for forming a second strand of DNA complementary to the template, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavably attached to the mass label, which mass label is uniquely resolvable in mass spectrometry for identifying the modified nucleotide, wherein each fragment is terminated with one of the probes, and wherein each set of mass labels from each set of four probes associated with each reaction vessel is different from the other sets of mass labels; and the fragments are pooled before step (ii).

5. A method according to claim 2, wherein the at least one template is a plurality of templates and the series of DNA fragments is provided by contacting each template in a separate reaction vessel in the presence of DNA polymerase with a mixture of nucleotides for hybridising to the template for forming a second strand of DNA complementary to the template, wherein the mixture further comprises a probe containing only one of the four nucleotides for hybridising to the template, the nucleotide of which probe comprises a modified nucleotide which is capable of polymerising to the second strand of DNA but blocked to prevent further polymerisation thereto, wherein each fragment is terminated with the probe and wherein either the primer or the modified nucleotide of the probe is cleavably attached to the mass label, which mass label is associated with the reaction vessel and uniquely resolvable in mass spectrometry from the mass label in the other reaction vessels for identifying the modified nucleotide used in the reaction vessel and the fragments are pooled before step (ii).

6. A method according to claim 2, wherein the at lease one template is a plurality of templates and the series of DNA fragments is provided by contacting the plurality of templates in each of four separate reaction vessels in the presence of DNA polymerase with a mixture of nucleotides for hybridising to the template for forming a second strand of DNA complementary to the template, wherein the mixture further comprises a probe containing in each of the reaction vessels only one of the four nucleotides for hybridising to the template, the nucleotide of which probe comprises a modified nucleotide which is capable of polymerising to the second strand of DNA but blocked to prevent further polymerisation thereto, wherein each fragment is terminated with the probe and wherein the primer is cleavably attached to the mass label, which mass label is associated with the primer and uniquely resolvable in mass spectrometry from the mass labels associated with the other primers used in the reaction zone; and wherein each nucleotide from its corresponding reaction vessel is related to its position in the template.

7. A method according to claim 2, wherein the at least one template is four sets of DNA single-stranded templates, each set comprising an identical plurality of DNA single-stranded templates and the series of DNA fragments is provided by contacting each set in a separate reaction vessel in the presence of DNA polymerase with a mixture of nucleotides for hybridising to the templates for forming a second strand of DNA complementary thereto, wherein the mixture further comprises a probe containing in each of the reaction vessels only one of the four nucleotides for hybridising to the template, the nucleotide of which probe comprises a modified nucleotide which is capable of polymerising to the second strand of DNA but blocked to prevent further polymerization thereto, wherein each fragment is terminated with the probe and wherein each of the templates of the four sets is primed with a primer to which the mass label is cleavably attached, which mass label which uniquely resolvable in mass spectrometry from the mass labels corresponding to the other templates and which is relatable to its respective template and its respective reaction vessel wherein the fragments are pooled before step (ii), and each nucleotide from its corresponding reaction zone is related to its position in the template.

8. A method according to claim 2, wherein the at least one template is a plurality of templates and the series of DNA fragments is provided by contacting each set of templates in a separate reaction vessel in the presence of DNA polymerase with a mixture of nucleotides for hybridising to the templates for forming a second strand of DNA complementary thereto, wherein the mixture further comprises a set of four probes containing all four nucleotides for hybridising to the template in which the nucleotide of each probe comprises a modified nucleotide which is capable of polymerising to the second strand of DNA but blocked to prevent further polymerisation thereto and which is cleavable attached to the mass label, which mass label is uniquely resolvable in mass spectrometry for identifying the modified nucleotide, wherein each fragment is terminated with one of the probes, and wherein each set of mass labels from each set of four probes associated with each reaction vessel is different from the other sets of mass labels and, before step (ii), the fragments are pooled and the pooled fragments are sorted according to a sub-sequence having a common length of 3 to 5 bases adjacent to the primer to form an array of groups of sorted fragments, wherein each group is spatially separated from the other groups.

9. A method according to claim 2, wherein the series of DNA fragments is provided by
(i) contacting the template in the presence of DNA polymerase with a mixture of nucleotides for hybridising to the template for forming a second strand of DNA complementary to the template, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;
(ii) removing unincorporated nucleotides;
(iii) unblocking the modified nucleotides; and
(iv) contacting the series of templates with an array of oligonucleotide probes, wherein each oligonucleotide probe has a nucleotide sequence of common length 2 to 6, all combinations of nucleotide sequences are present in the array, and wherein each probe is cleavably attached to the mass label, which mass label is uniquely resolvable in mass spectrometry for identifying the nucleotide sequence.

10. A method according to claim 2, wherein the at least one template is a plurality of primed DNA single-stranded templates, each at a unique concentration, and the series of DNA fragments is provided by
(i) contacting the templates in the presence of DNA polymerase with a mixture of nucleotides for hybridising to the template for forming a second strand of DNA complementary to the templates, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;

(ii) removing unincorporated nucleotides;

(iii) unblocking the modified nucleotides; and (iv) contacting the series of templates with an array of oligonucleotide probes, wherein each oligonucleotide probe has a nucleotide sequence of common length 2 to 6, all combinations of nucleotide sequences are present in the array, and wherein each probe is cleavably attached to the mass label, which mass label is uniquely resolvable in mass spectrometry for identifying the nucleotide sequence.

11. A method according to claim 2, wherein the series of DNA fragments is provided by contacting the template in the presence of DNA ligase with a mixture of oligonucleotides for hybridising to the template for forming a second strand of DNA complementary to the template, the oligonucleotides each having a common length in the range 2 to 6, wherein the mixture further comprises a set of probes containing all possible oligonucleotides of the common length L for hybridising to the templates in which the oligonucleotide of each probe comprises a modified oligonucleotide which is capable of ligating to the second strand of DNA but blocked to prevent further ligation thereto and which is cleavable attached to the mass label, which mass label is uniquely resolvable in mass spectrometry for identifying the modified oligonucleotide, and the series of fragments contains all possible lengths of the second strand of DNA of integer multiples of L in which each fragment is terminated with one of the probes.

12. A method according to claim 2, wherein the at least one template is a plurality of primed DNA single-stranded templates, each at a unique concentration, and the series of DNA fragments is provided by contacting the templates in the presence of DNA ligase with a mixture of oligonucleotides for hybridising to the templates for forming a second strand of DNA complementary to the templates, the oligonucleotides each having a common length in the range 2 to 6, wherein the mixture further comprises a set of probes containing all possible oligonucleotides of the common length L for hybridising to the templates in which the oligonucleotide of each probe comprises a modified oligonucleotide which is capable of ligating to the second strand of DNA but blocked to prevent further ligation thereto and which is cleavably attached to the mass label, which mass label is uniquely resolvable in mass spectrometry for identifying the modified oligonucleotide, and the series of fragments contains all possible lengths of the second strand of DNA of integer multiples of L in which each fragment is terminated with one of the probes.

13. A method according to claim 5, wherein the plurality of single-stranded templates is primed by hybridising to a known sub-sequence common to each of the templates an array of primers each comprising a base sequence containing a common sequence complementary to the known sub-sequence and a variable sequence of common length, in the range of 2 to 6, in which the array contains all possible nucleotide sequences of that common length and the mass label cleavably attached to each primer identifies the variable sequence, which variable sequence identifies the template to be sequenced.

14. A method according to claim 8, wherein the step of sorting the pooled fragments comprises contacting the fragments with an array of spatially separate oligonucleotides each comprising a base sequence containing a common sequence complementary to the primer sequence of the fragments and a variable sequence of the common length, which array contains all possible variable sequences of the common length.

15. A method according to claim 4, wherein the reaction zones are separate containers.

16. A method according to claim 3, wherein the mixture of nucleotides comprises ATP, TTP, CTP and GTP.

17. A method according to claim 2, wherein the modified nucleotides are dideoxy- or deoxynucleotides.

18. A method according to claim 2, wherein the primed DNA is immobilised on a solid support.

19. A method according to claim 1, wherein each mass label is cleavably attached to a fragment by a linker cleavable in a mass spectrometer.

20. A method for characterising DNA, which comprises (a) providing a primed DNA single-stranded template;

(b) contacting the template in the presence of DNA polymerase with a mixture of nucleotides for hybridising to the template for forming a second strand of DNA complementary to the template, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;

(c) removing unincorporated nucleotides;

(d) unblocking the modified nucleotides;

(e) contacting the series of templates with an array of oligonucleotide probes to form a series of fragments, each oligonucleotide probe having a nucleotide sequence of common length 2 to 6, and all combinations of sequences being present in the array, wherein each probe is cleavably attached to a mass label uniquely resolvable in mass spectrometry for identifying the nucleotide sequence;

(f) separating the fragments by capillary electrophoresis, thereby determining the length of each fragment;

(g) cleaving each fragment by collision to release its mass label; and (h) determining each mass label by mass spectrometry to relate a nucleotide sequence that corresponds to the mass label to a position in the template so as to deduce the sequence of the template in order to characterise the DNA.

21. A method for characterising DNA, which comprises (a) providing a plurality of primed DNA single-stranded templates, each at a unique concentration;

(b) contacting the templates in the presence of DNA polymerase with a mixture of nucleotides for hybridising to the template for forming a second strand of DNA complementary to the templates, wherein the mixture further comprises a set of four probes containing all four nucleotides for hybridising to the templates in which the nucleotide of each probe comprises a modified nucleotide which is capable of polymerising to the second strand of DNA but reversibly blocked to prevent further polymerisation thereto, wherein the step of contacting forms a series of templates containing all possible lengths of the second strand of DNA, each second strand terminated with one of the probes;

(c) removing unincorporated nucleotides;

(d) unblocking the modified nucleotides;

(e) contacting the series of templates with an array of oligonucleotide probes to form a series of fragments, each oligonucleotide probe having a nucleotide sequence of common length 2 to 6, and all combinations of sequences being present in the array, wherein each probe is cleavably attached to a mass label uniquely resolvable in mass spectrometry for identifying the nucleotide sequence;

(f) separating the fragments by capillary electrophoresis, thereby determining the length of each fragment;

(g) cleaving each fragment by collision to release its mass label; and (h) determining the identity and amount of each mass label by mass spectrometry to relate a nucleotide sequence of a probe that corresponds to the mass label to a position in its respective template so as to deduce the sequence of the template in order to characterise the DNA.

22. A method for characterising DNA, which comprises (a) providing a primed DNA single-stranded template;

(b) contacting the template in the presence of DNA ligase with a mixture of oligonucleotides for hybridising to the template for forming a second strand of DNA complementary to the template, the oligonucleotides each having a common length in the range 2 to 6, wherein the mixture further comprises a set of probes containing all possible oligonucleotides of the common length L for hybridising to the templates in which the oligonucleotide of each probe comprises a modified oligonucleotide which is capable of ligating to the second strand of DNA but blocked to prevent further ligation thereto and which is cleavably attached to a corresponding mass label uniquely resolvable in mass spectrometry for identifying the modified oligonucleotide, wherein the step of contacting forms a series of fragments containing all possible lengths of the second strand of DNA of integer multiples of L, each fragment terminated with one of the probes;

(c) separating the fragments by capillary electrophoresis, thereby determining the length of each fragment;

(d) cleaving each fragment by collision to release its mass label; and (e) determining each mass label by mass spectrometry to relate its corresponding oligonucleotide to a position in the template so as to deduce the sequence of the template in order to characterise the DNA.

23. A method for characterising DNA, which comprises (a) providing a plurality of primed DNA single-stranded templates, each at a unique concentration;

(b) contacting the templates in the presence of DNA ligase with a mixture of oligonucleotides for hybridising to the templates for forming a second strand of DNA complementary to the templates, the oligonucleotides each having a common length in the range 2 to 6, wherein the mixture further comprises a set of probes containing all possible oligonucleotides of the common length L for hybridising to the templates in which the oligonucleotide of each probe comprises a modified oligonucleotide which is capable of ligating to the second strand of DNA but blocked to prevent further ligation thereto and which is cleavably attached to a corresponding mass label uniquely resolvable in mass spectrometry for identifying the modified oligonucleotide, wherein the step of contacting forms a series of fragments containing all possible lengths of the second strand of DNA of integer multiples of L, each fragment terminated with one of the probes;

(c) separating the fragments by capillary electrophoresis, thereby determining the length of each fragment;

(d) cleaving each fragment by collision to release its mass label; and (e) determining the identity and amount of each mass label by mass spectrometry to relate its corresponding oligonucleotide to a position in its respective template so as to deduce the sequence of the template in order to characterise the DNA.

24. A method for characterizing DNA, which comprises:

(a) providing at least one DNA single-stranded template primed with a primer;

(b) generating a population of fragments of said DNA from the at least one template by contacting the at least one template in the presence of DNA polymerase with a mixture of nucleotides for hybridising to the at least one template for forming a second strand of DNA complementary to the at least one template, wherein the mixture further comprises a set of four probes containing all four nucleotides for hybridising to the at least one template in which the nucleotide of each probe comprises a modified nucleotide or oligonucleotide which is capable of polymerising to the second strand of DNA but blocked to prevent further polymerisation thereto, which modified nucleotide or oligonucleotide is cleavably attached to the mass label for identifying the modified nucleotide or oligonucleotide, which mass label is cleavable from the probe in a mass spectrometer and is resolvable by mass spectrometry, and wherein each fragment is terminated with one of the probes, wherein the population comprises at least one series of DNA fragments, the series containing all possible lengths of a second strand of DNA complementary to the or each template;

(c) separating the fragments by capillary electrophoresis, thereby determining the length of each fragment;

(d) cleaving each fragment in a mass spectrometer by collision to release its mass label; and (e) determining each mass label by mass spectrometry identify a terminating modified nucleotide or oligonucleotide of each fragment by the length of the fragment in order to characterize said DNA.

* * * * *